(12) United States Patent
Pile-Spellman et al.

(10) Patent No.: US 10,363,364 B2
(45) Date of Patent: Jul. 30, 2019

(54) DEVICES FOR ESTIMATING REGIONAL METABOLIC RATE OF ORGANS BASED ON HEAT GENERATION AND FOR ESTIMATING REGIONAL BLOOD FLOW(S) FOR THE VOLUME(S) OF TISSUE PERFUSED

(71) Applicant: Hybernia Medical LLC, Pelham, NY (US)

(72) Inventors: John Pile-Spellman, Pelham, NY (US); Jae H. Choi, Mineola, NY (US)

(73) Assignee: Hybernia Medical LLC, New Rochelle, NY (US)

( * ) Notice: Subject to any disclaimer, the term of this patent is extended or adjusted under 35 U.S.C. 154(b) by 270 days.

(21) Appl. No.: 14/996,370

(22) Filed: Jan. 15, 2016

(65) Prior Publication Data
US 2016/0206816 A1    Jul. 21, 2016

Related U.S. Application Data

(60) Provisional application No. 62/103,868, filed on Jan. 15, 2015.

(51) Int. Cl.
*A61M 5/172*    (2006.01)
*A61M 5/168*    (2006.01)
(Continued)

(52) U.S. Cl.
CPC ........... *A61M 5/1723* (2013.01); *A61B 5/028* (2013.01); *A61F 7/12* (2013.01); *A61M 5/16804* (2013.01);
(Continued)

(58) Field of Classification Search
CPC ............ A61M 5/1723; A61M 2205/52; A61M 2205/3606; A61M 2205/3368; A61M 2230/50; A61B 5/4866; A61B 5/4848; A61B 5/4064; A61B 5/01; A61F 7/12; A61F 2007/0063; A61F 2007/126; A61F 2007/0095; A61F 2007/0059
See application file for complete search history.

(56) References Cited

U.S. PATENT DOCUMENTS

| 2004/0116987 A1* | 6/2004 | Magers ..................... A61F 7/12 607/105 |
| 2008/0017194 A1* | 1/2008 | Hassanein ................ A01N 1/02 128/200.24 |

(Continued)

*Primary Examiner* — Nathan R Price
*Assistant Examiner* — Anh Bui
(74) *Attorney, Agent, or Firm* — Antonio Papageorgiou; Meister Seelig & Fein LLP

(57) ABSTRACT

The present application provides systems that include a controller, and an insertion device with at least one temperatures sensor thereon and a pump coupled to the controller. The insertion device provides temperature measurement(s) at/of a subject's organ to the controller and the controller varies an infusate flow rate to induce temperature changes in at least a portion of the subject's organ and stores the temperature measurements during perfusion induced temperature changes on a memory device. The controller may estimate at least one hemodynamic characteristic of at least a portion of the subject's organ based on the temperature measurements obtained during perfusion induced temperature changes.

19 Claims, 19 Drawing Sheets

(51) Int. Cl.
*G06F 19/00* (2018.01)
*A61B 5/028* (2006.01)
*G16H 50/50* (2018.01)
*A61F 7/00* (2006.01)
*A61F 7/12* (2006.01)
*A61M 5/142* (2006.01)
*A61B 5/01* (2006.01)
*A61B 5/026* (2006.01)
*A61B 5/00* (2006.01)

(52) U.S. Cl.
CPC .......... *G06F 19/00* (2013.01); *G06F 19/3468* (2013.01); *G16H 50/50* (2018.01); *A61B 5/01* (2013.01); *A61B 5/026* (2013.01); *A61B 5/4064* (2013.01); *A61B 5/4845* (2013.01); *A61B 5/4848* (2013.01); *A61B 5/4866* (2013.01); *A61F 2007/0059* (2013.01); *A61F 2007/0063* (2013.01); *A61F 2007/0095* (2013.01); *A61F 2007/126* (2013.01); *A61M 2005/14208* (2013.01); *A61M 2005/1726* (2013.01); *A61M 2205/3303* (2013.01); *A61M 2205/3368* (2013.01); *A61M 2205/3606* (2013.01); *A61M 2205/52* (2013.01); *A61M 2230/04* (2013.01); *A61M 2230/50* (2013.01)

(56) References Cited

U.S. PATENT DOCUMENTS

| | | | | |
|---|---|---|---|---|
| 2008/0249388 | A1* | 10/2008 | Kumhyr | A61B 5/00 600/368 |
| 2009/0043366 | A1* | 2/2009 | Dae | A61F 7/0085 607/113 |
| 2013/0030411 | A1* | 1/2013 | Kreck | A61F 7/12 604/514 |
| 2013/0331916 | A1* | 12/2013 | Pile-Spellman | A61F 7/12 607/106 |
| 2014/0243738 | A1* | 8/2014 | Kramer | A61M 5/1407 604/67 |

* cited by examiner

Temperature and Cerebral Blood flow in normal brain hemisphere

Temperature and Cerebral Blood flow in ischemic penumbra

Temperature and Cerebral Blood flow in normal + ischemic penumbra

DEVICES FOR ESTIMATING REGIONAL METABOLIC RATE OF ORGANS BASED ON HEAT GENERATION AND FOR ESTIMATING REGIONAL BLOOD FLOW(S) FOR THE VOLUME(S) OF TISSUE PERFUSED

BACKGROUND OF THE INVENTION

The present application relates to systems and methods for estimating regional metabolic rate and blood flows of a subject's organ during endovascular interventions.

More particularly, This application describes useful and novel ways to continuously, practically, intra-operatively estimate canonical vascular physiological variables, (Regional Cerebral Blood Flow (rCBF), Regional Cerebral Metabolic Rate (rCMR), Regional Cerebral Vascular Resistance (rCVR), Regional Cerebral Perfused Volume (rCPV)) and; to calculate from these, estimates for recognized (cerebral autoregulation) or new key patho-physiological thresholds (Perfusion Sparing Threshold (PST) (specifically for temperature, Partial Arterial Oxygen Pressure (PaO2), Mean Arterial Pressure (MAP)) and/or new vascular biomarkers, (Reperfusion Severity Index (RSI), Reperfusion Hyperemia Index (RHI)). These values can also be used to determine, and be manipulated for optimal intra-arterial hypothermia and drug delivery. The described application focuses on brain, although the methods described would also work for other organs such as heart and kidneys.

Metabolic rate refers to the rate at which metabolism occurs in living organisms. The metabolic rate of an organ, such as the brain, is generally the rate that the organ uses fuel, oxygen, glucose, etc. Although the brain represents about 2% of total body weight, it consumes between 10-20% of the total oxygen delivered in the resting body. Moreover, unlike other organs, the brain as a whole doesn't have a "resting" state. Rather, the brain is considered to be constantly "active."

The cerebral rate of oxygen metabolism (CMRO2) of a normal, conscious individual is generally known. The rCBF of a normal, conscious individual is also generally known. Deviations from the norm or from a reference rate may be probative of the relative health of the brain. In this regard, a number of procedures have been proposed to estimate metabolic rates in the brain and/or rCBF using imaging systems, such as positron emission computed tomography (PET), Single Photon Emission Computed Tomography (SPECT), and magnetic resonance imaging (MRI). One such procedure is discussed in U.S. Patent Publication No. 20090198122 entitled "Systems and Methods for Determining Metabolic Rate Using Temperature Sensitive Magnetic Resonance Imaging", which is incorporated herein by reference. Imaging systems, however, have their drawbacks when it comes to determining metabolic rates and blood flows. Particularly, imaging systems generally only provide a "snapshot" of an organ's metabolic rate at a given time. Repetitive scans are typically not practical or economical, and therefore do not provide an adequate solution. Moreover, these imaging systems cannot be used during endovascular interventions without significantly delaying or interrupting the therapy.

Additionally, almost all drugs are given by oral, intravenous, or dermal routes. Towering experience, expertise, daunting IP, and breathtaking amounts of effort have been marshalled to effectively address the myriad of issues to craft drugs and carriers that can be given in this fashion. Vascular endothelial toxicity is problematic in many drugs, irrespective of how given, and is thought to account for a significant amount of short term and long term morbidity associated with drug treatment. Accordingly, there is a need for systems and corresponding procedures for administering drugs that control their toxicity, ergo their effects on non-target tissue. Additionally correct drug dosing during intra-arterial drug delivery is challenging without knowledge of the regional blood flow, volume of tissue being perfused, and energy metabolism. Accordingly, there is a need for systems and corresponding procedures for using such systems that are not so limited and/or otherwise address one or more of the issues noted above.

SUMMARY OF THE INVENTION

The systems and corresponding procedures for using the systems disclosed herein aim to address one or more of the following issues associated with the current diagnostic paradigm in acute ischemic stroke: (1) Imaging systems only provides an incomplete "snapshot" of the processes involved in ischemic tissue damage; (2) Repetitive brain imaging or monitoring during reperfusion therapy is not practical or economical; and (3) In patients selected for endovascular recanalization therapy (ERT), further assessments of organ physiology and ischemic damage cannot be performed during the entire intervention.

Moreover, it is noteworthy that tissue death or survival has never been assessed (using these systems or otherwise) based on a measured or estimated metabolic rate. Accordingly, the systems and corresponding procedures disclosed herein may provide practical and economical methods to monitor, for example, changes in regional blood flow and regional organ metabolism in an angiographic setting. This may lead to improved patient selection, help guide treatment, reduce occurrence of secondary injuries (hemorrhage, reperfusion injury, inflammation), support individualized care, and/or result in more effective interventions and better patient outcome. Moreover, to the extent that regional organ blood flow and regional metabolism may be manipulated, the system and corresponding procedures may be used to influence variables associated with intra-arterial drug delivery, including extraction fraction, drug metabolism and, local drug toxicity.

Accordingly, in at least one aspect, a system is provided that includes a controller; an insertion device comprising at least one temperatures sensor thereon, the insertion device functionally coupled to the controller to provide at least one temperature measurement of a subject's organ to the controller; a pump functionally coupled to the controller for the controller to vary an infusate flow rate to induce temperature changes in at least a portion of the subject's organ; and a memory device functionally coupled to the controller, the controller operable to store the at least one measure of the temperature of an organ to the controller during perfusion induced temperature changes in at least a portion of the subject's organ, and further operable to estimate at least one hemodynamic characteristic of at least a portion of the subject's organ based on the at least one temperature measurement obtained during perfusion induced temperature changes.

In at least one embodiment, the at least one hemodynamic characteristic comprises a metabolic rate of at least a portion of the subject's organ.

In at least one embodiment, the at least one hemodynamic characteristic comprises a tissue blood flow rate associated with at least a portion of the subject's organ.

In at least one embodiment, the at least one hemodynamic characteristic comprises heat production associated with at least a portion of the subject's organ.

In at least one embodiment, the controller is operable to vary an infusate flow rate to lower the temperature in at least a portion of the subject's organ.

In at least one embodiment, the controller is operable to vary an infusate flow rate to maintain at least a portion of the subject's organ at an equilibrium temperature below normal.

In at least one embodiment, the controller is operable to vary an infusate flow rate to incrementally lower and decrease the temperature of at least a portion of the subject's to a plurality of different equilibrium temperatures, and to maintain the temperature of at least a portion of the subject's organ to each of the plurality of equilibrium temperatures.

In at least one embodiment, the at least one hemodynamic characteristic is estimated based on a plurality of temperature measures during perfusion induced temperature changes comprising at least one wash-in, equilibrium, and wash-out cycle.

In at least one embodiment, the at least one hemodynamic characteristic comprises at least one of metabolic rate, a tissue blood flow rate, heat production of at least a portion of the subject's organ.

In at least one embodiment, the at least one hemodynamic characteristic comprises perfused volume of tissue.

In at least one embodiment, the at least one hemodynamic characteristic comprises perfused volume of penumbra tissue.

In at least one embodiment, the perfused volume of penumbra tissue is estimated as a function of a product of infusate rate and temperature at an initial time and at equilibrium.

In at least one embodiment, the at least one hemodynamic characteristic comprises blood flow associated with a perfused volume of tissue.

In at least one embodiment, the at least one hemodynamic characteristic comprises blood flow associated with a perfused volume of penumbra tissue.

In at least one embodiment, the at least one hemodynamic characteristic comprises a penumbra sparing threshold temperature.

In at least one embodiment, the at least one hemodynamic characteristic comprises a reperfusion hyperemia index.

In at least one embodiment, the at least one hemodynamic characteristic comprises a reperfusion severity index.

In at least one embodiment, the controller further operable to display an interface screen comprising the at least one hemodynamic characteristic associated with at least a portion of the subject's organ.

In at least one embodiment, the interface screen comprises a real time display of at least one of infused volume of normal tissue and infused volume of penumbra tissue.

Additional aspects of the present invention will be apparent in view of the description which follows.

DETAILED DESCRIPTION OF THE INVENTION

Figure 1A:
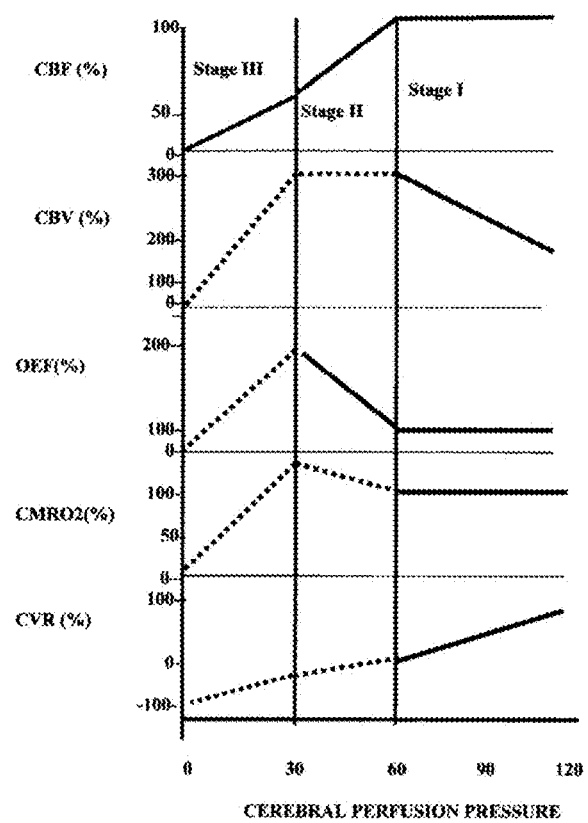
FIGS. 1A and 1B depict graphs that chart physiological variables of the brain against cerebral perfusion pressure (CPP).

The present application generally provides systems and corresponding procedures for estimating and/or manipulating canonical vascular physiological variables, such as metabolic rates, as well as other physiological variables, in one or more of a subject's organs, such as the subject's brain or any portion thereof. More particularly, this application provides systems and procedures for determining regional tissue heat production, and tissue blood flow(s) for infused tissues of a subject's organs during, e.g., arterial endovascular interventions, and calculating/estimating there from recognized and new key patho-physiological thresholds. Additionally, this application provides systems and procedures for controlling variables associated with intra-arterial drug delivery, such as blood flow, drug concentration, and metabolic rates, thereby influencing extraction fraction, drug metabolism, and local drug toxicity.

The term endovascular intervention denotes any medical or surgical procedure that involves intraluminal access of a subject's vasculature. Endovascular interventions therefore include procedures that are performed intraluminally, such as hypothermic therapy, endovascular thrombolysis, recanalization, embolization, angioplasty, stenting, etc., as well as those procedures that entail at least some degree of intraluminal activity, such as targeted delivery of therapeutic agents and those involving intraluminal navigation to access a site targeted for the intervention. Moreover, the interventions are not limited to therapeutic procedures and may therefore include diagnostic procedures. Although the systems and procedures of the present disclosure may be discussed by way of example in relation to certain organs, such as the brain, it is understood that these systems and procedures may be used in relation to other organs or any portions thereof.

The brain metabolizes oxygen (O2) and glucose (Glu) to produce sufficient energy for the cellular processes in the form of ATP (adenosine tri phosphate) under aerobic conditions. The process can be described by the following: Glu+6O2→6CO2+6H2O. One third of the enthalpy from this process dissipates into heat and two thirds are used to produce 38 ATP molecules. Since nutrients are carried in blood, blood flow, arterial oxygen content, and oxygen extraction are some of the essential factors that ensure a sufficient supply of nutrients to the cells. In the brain, cerebral oxygen metabolism (CMRO2) can be determined from the cerebral blood flow (CBF) and oxygen extraction fraction (OEF). In end stage flow limiting situations, these variables, CBF, OEF, determine the CMR. CBF serves not only to supply nutrients to the brain, but also to remove heat that is produced by its energy metabolism. This is an important function of CBF as the brain cannot dissipate heat to the outside environment well due to the surrounding skull. Normal values of these and other physiological variables for the human brain are provided in Table A.

TABLE A

| | |
|---|---|
| CBF | 45-67 ml/100 g brain tissue*min (~800 ml/whole brain @ 1,400 g) |
| CMRO2 | 3.5-3.9 ml O2/100 g brain tissue*min or 150 μmol O2/100 g*min |
| Cerebral glucose utilization [CMRglu] | 5.5 mg Glu/100 g brain tissue*min |
| OEF | 44.5% |
| Energy equivalent total brain | 20 W or 0.25 kcal/min |
| ATP turnover rate total brain | 7 mmol/min or $4*10^{21}$ molecules/min |
| Heat production | 66 J/100 g brain tissue*min |

Figure 1B:
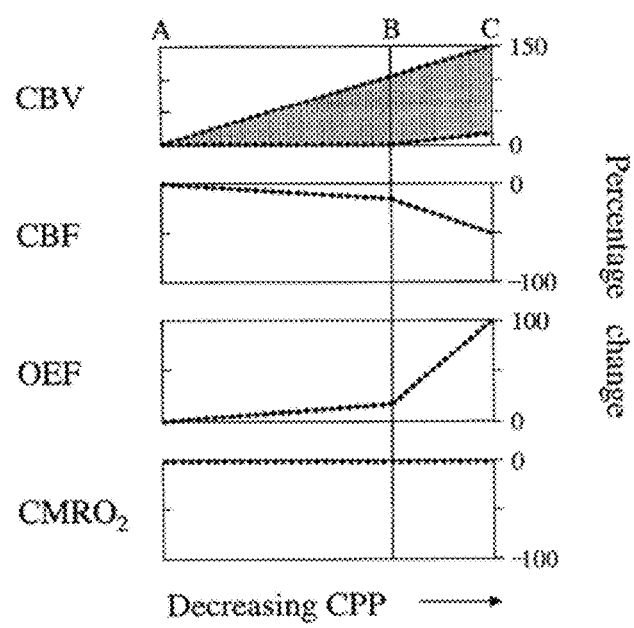

When an artery that supplies a part of the brain with blood is blocked, e.g., by a blood clot, ischemic stroke might ensue. In chronic conditions, e.g., carotid artery disease, it has been shown that two compensation mechanisms exist in the brain to maintain physiological energy metabolism and to prevent ischemic injury. The first is dilation of the arteries (decrease in cerebrovascular resistance or CVR) in the affected region to improve CBF (Stage I)). As a result, cerebral blood volume (CBV) will increase. With further loss of CBF due to decreasing cerebral perfusion pressure (CPP), a second mechanism is activated, i.e., increased OEF (Stage II). Prolonged failure of Stage II will result in ischemic injury (Stage III). FIGS. 1A and 1B illustrate in graphical form the changes in these physiological variables with the progressive increase/decrease in perfusion pressure. Accordingly, measuring and/or monitoring one or more of these variables may provide valuable insight with regard to the hemodynamic stage of the brain, for example, after a subject has experienced an acute ischemic stroke. Moreover, one or more of these variables may be manipulated purposely to influence intra-arterial drug delivery, including extraction fraction, drug metabolism, and local drug toxicity.

Accordingly, the present application provides systems and corresponding procedures for estimating one or more of the vascular physiological variables of an organ, such as the brain, based on heat produced by the particular organ at a given temperature. More particularly, the application provides systems and procedures for estimating metabolic rates, such as CMRO2, CMRglu, and CMRdrug (collectively "CMR"), CBF, CBV, CPP, CVR, RPV, PST, PaO2, MAP, RSI, RHI, etc., regional or otherwise, based on heat production of the brain, and for manipulating such variables to influence intra-arterial drug delivery. The present application also provides systems and corresponding procedures for controlling at least one of blood flow, drug concentration, and tissue metabolic rate of a particular organ, based on controlling at least one of drug dosage, infusate temperature, CBF, and hematocrit (Hct).

Heat produced by the brain or any part thereof may be estimated in a variety of ways. In at least one embodiment, heat production is estimated, using the systems disclosed herein, based on the measure of heat transferred to and/or from the brain and/or the timing thereof during perfusion induced temperature changes, including perfusion induced lowering of the temperature of the brain (cooling), preferably incrementally; maintaining the brain at a constant temperature (equilibrium), preferably at a temperature below normal or a reference temperature; and/or inducing or allowing the temperature of the brain to rise (heating), preferably incrementally. Perfusion may be performed using any biocompatible fluid (infusate), including blood, saline, drugs or generally any therapeutic agent, etc., or any combination thereof.

Figure 2:
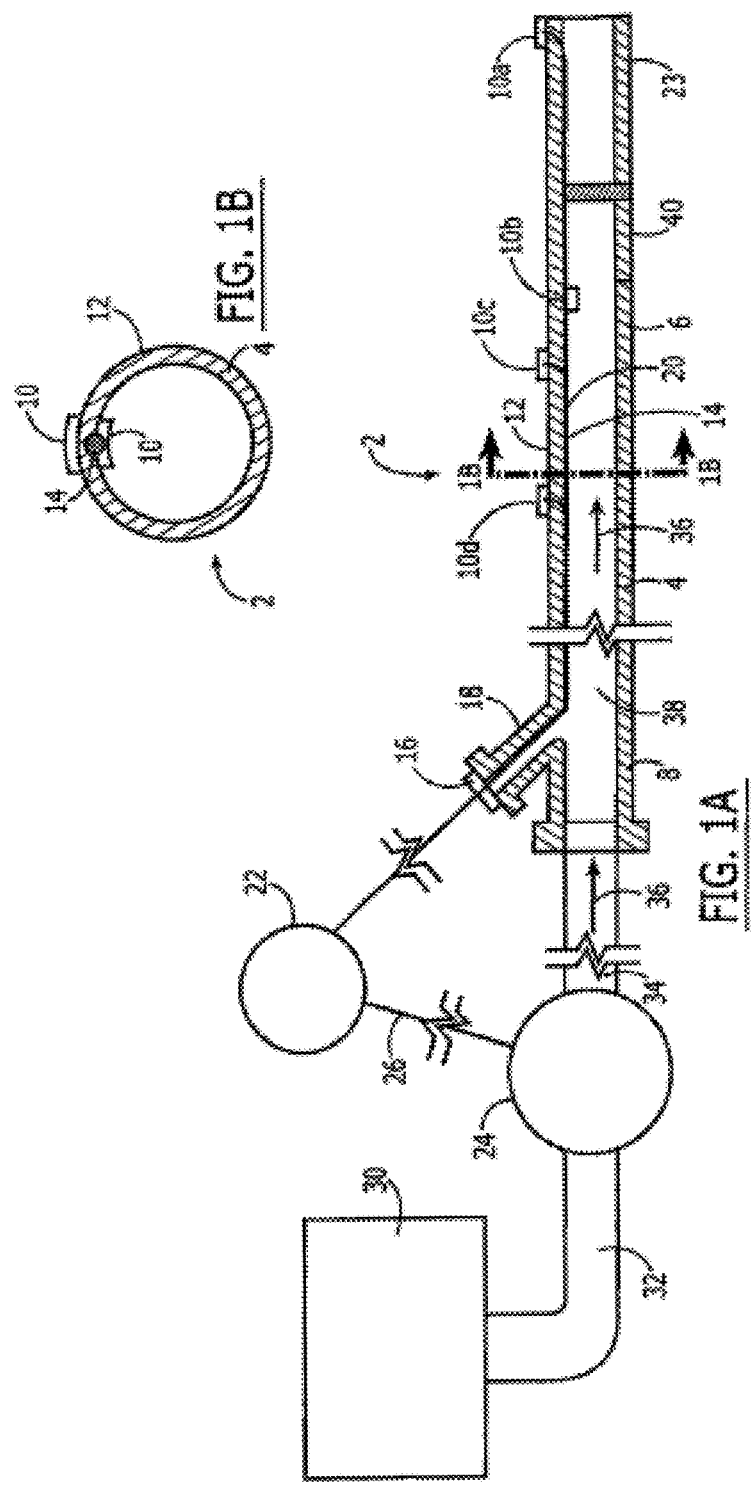
FIG. 2 depicts a system for use in estimating metabolic rate of an organ according to at least one embodiment of the systems discussed herein.

Heat transfer to and from the brain during perfusion may be measured/manipulated using a variety of systems, including the systems disclosed in U.S. Patent Publication No. 20090018504 entitled "System and Method for Intravascular Cooling", which is hereby incorporated herein. Referring to FIG. 2, in at least one embodiment, the system includes an insertion device 2, such as a catheter, having a distal end 6 and a proximal end 8. The insertion device 2 is generally a slender member that is inserted into a subject, e.g., the subject's femoral artery, with the distal end 6 first. The insertion device 2 includes one or more sensors 10a, 10b, 10c, 10d along an inner surface 20 (in the event that the insertion device 2 is a catheter) and/or outer surface 40 of the insertion device 2, which are electrically coupled to a controller 22 via wire(s) 14.

Various sensors may be incorporated onto or otherwise associated with the insertion device 2, including one or more temperature sensors, flow rate sensors, Hct sensors, etc. In the event that the insertion device 2 is a catheter, the insertion device 2 includes a longitudinally extending tubular member 4 with an opening at the proximal end 8 and an opening at the distal end 6. The opening at the distal end 6 represents the exit for the infusate. In at least one embodiment, the insertion device 2 is a catheter having a plurality of temperature sensors, including a temperature sensor within the lumen of the catheter 10b, and at least one temperature sensor outside of the catheter, for example, a sensor 10a at the distal end of the catheter or sensors 10b, 10c proximal relative to sensor 10b. Sensor 10b generally provides the temperature of the infusate within the catheter, 10c and 10d the arterial temperature, and 10a the temperature of the infusate and arterial blood mixture at the distal end of the catheter 2. In this regard, heat production may be determined based on the temperature readings with the one or more sensors, which provide temperatures T1-T4 as discussed herein. The catheter 2 is preferably insulated so as to limit heat transfer between the arterial blood and the infusate up to the distal end 6 of the catheter 2.

The controller 22 is preferably further coupled to an input device, such as a switch(es), rotary dial(s), keypad or keyboard, touch screen, etc. and an output device, such as a monitor, printer, etc. The input device generally provides an interface for users to specify and adjust the operating parameters of the system, such as infusate temperature, infusate flow rate, time, drug dosage, Hct, etc., and the output device provides one or more interfaces for presenting to the user data obtained, e.g., from the one or more sensors 10a, 10b, 10c, 10d, and/or data computed by the system based on such data obtained. The data computed preferably includes estimates of the physiological variables noted herein, which may be presented individually, in tabular form, and/or in the form of a graphical representations of the data, e.g., over time. The output device may be a display, such as an LCD monitor, a printer, etc. The system may further store one or more predefined sets of instruction with regard to temperature, flow rate, time, drug dosage, hematocrit, etc. in a computer memory device, which may be implemented by the system upon selection by the user. As discussed herein, the system may estimate heat production of an organ based on heat transferred to and from the organ during perfusion induced temperature changes and/or during equilibrium. In this regard, the sets of instruction may include sequence and timing for the operating parameters of the system, for example, for incrementally cooling, maintaining temperature, inducing or allowing temperature of an organ to rise, controlling Hct and flow rates, etc. The memory may further store the data collected and/or estimated by the system, for example, in a database.

The controller 22 is further coupled to the pump 24 and/or at least one infusate reservoir 30, for example, through one or more wires 26 to control the operation of the pump 24 and/or reservoir 30 with regard to, for example, infusate flow rate, temperature, drug dosage, Hct, etc. Any pump, such as a blood pump, with a wide dynamic range, e.g., from about 2 cc/min to about 360 cc/min, may be used for pump 24. Similarly, any reservoir 30 may be used to supply the infusate, e.g., for perfusion induced temperature changes as discussed herein; however, the reservoir 30 preferably provides infusate at a controlled temperature, which may be cooled, heated and/or maintained by the controller 22 at any desired temperature ranging from about −10° C. to about 40° C. As shown in the FIG. 2, the pump 24 generally draws cooled and/or heated infusate from a reservoir 30 via inlet 32 and expels the infusate at the desired flow rate via outlet 34 into the lumen 38 in the insertion device 2. The flow rate and/or temperature may be controlled by the controller 22 based on data obtained from the one or more sensors 10a, 10b, 10c, 10d, and/or data computed by the system based on such data obtained. That is, the controller 22 may vary the operation of the pump 24 and/or the reservoir 30 to maintain the desired temperature, flow, physiological parameters, etc., at any given time.

Figure 3:
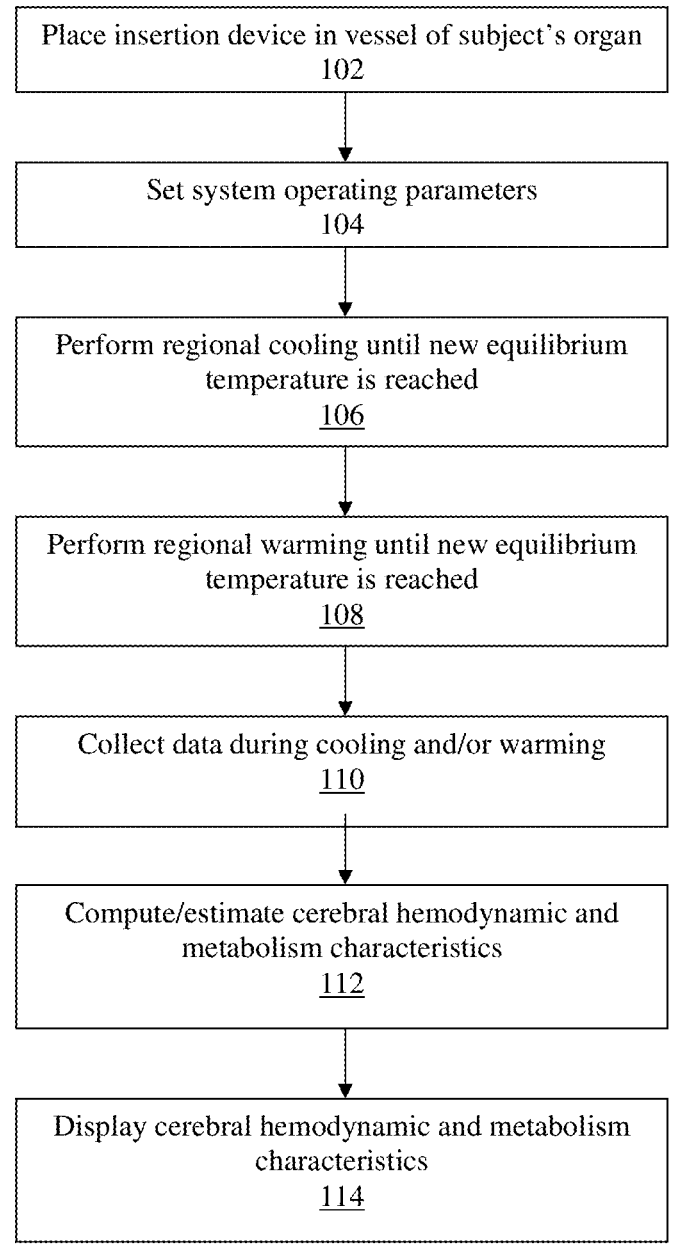
FIG. 3 depicts a flow diagram of a process for use in estimating metabolic rate of an organ according to at least one embodiment of the processes discussed herein.

As indicated above, heat production may be estimated, using the systems disclosed herein, based on the measure of heat transferred to and/or from the brain and/or the timing thereof during perfusion induced temperature changes. In this regard, the system is operable to induce and measure heat transfer during at least one of: 1) lowering of the temperature of the brain (cooling), preferably incrementally; 2) maintaining the brain at a constant temperature (equilibrium), preferably at a temperature below normal or a reference temperature; and 3) rising of the temperature of the brain, preferably incrementally. Referring to FIG. 3, in one embodiment, the system induces temperature changes in one or more sequences generally referred to as "wash-in" and "wash-out" techniques, during cooling and rewarming respectively, with equilibrium referring to the time that the brain is kept at a constant temp with minimal changes in cooling. The wash-in technique generally begins by placing the insertion device 2, e.g., a catheter, into the vessel of the territory to be interrogated 102. For example, the catheter may be inserted into the subject's femoral artery and navigated to one of the carotid arteries for interrogation of the subject's brain. Once in place, the operating parameters of the system and any safety variables may be set 104 (e.g., to prevent a body temperature drop over 1 to 1.5 degrees Celsius, whole body hematocrit drop below 25, and/or prevent against fluid overload). In one embodiment, the operating parameters that are set include at least one of infusate temperature, arterial blood/infusate mix temperature, and infusate flow rate. The set temperature(s) will generally be below the body temperature of the subject, preferably low enough to collect a sufficient set of data for a better resolution of the physiological parameter estimates that follow. For example, the temperature may be set to 5 degrees C. below the body temperature. Once the temperature is set, regional cooling may be performed at the set infusate rate until the brain reaches a new temperature equilibrium for native vessel flow rate 106. The equilibrium temperature may be maintained for any desired period of time. Moreover, the equilibrium may be set based on a new fixed infusion rate, which is a fraction (about ⅓) of the infusion rate at the previous equilibrium. As indicated herein, the induced temperature changes in the organ may influence at least one of extraction fraction, drug metabolism and, local drug toxicity. In this regard, the system may be set to reduce the temperature of the organ to achieve the desired changes with regard to these intra-arterial drug delivery variables, followed by intra-arterial drug delivery.

The "wash-out" technique generally includes the "wash-in" technique's cooling and maintaining the new temperature equilibrium for the brain describe above, with the addition of warming of the brain 108. Warming may be induced by perfusing infusate at a temperature higher than the equilibrium temperature and/or simply reducing the infusate flow sufficient to allow arterial blood flow to warm the brain on its own. The wash-in and wash-out steps may be repeated in stages, for example, to achieve incremental increase/decreases in the equilibrium temperatures. The system generally collects the relevant data 110, such as admixture (arterial blood and infusate) and infusate flow rates, temperature, volume, etc. in real time (during the intervention) and stores the information in the computer memory for processing, which is preferably also performed in real time. Finally, the data collected may be processed to compute or otherwise estimate cerebral hemodynamic and metabolism characteristics (as discussed herein) 112 and the computed/estimated characteristics may be displayed on an interface screen 114, such as the interface screen shown in FIG. 6.

As noted above, the changes in the temperature and the rate of temperature change logged by the system provide data with regard to the physiology of the brain. That is, the major factor of heat transfer to and from tissue(s) of the brain is bulk blood flow, which may effectively be modeled by Pennes' "heat flux" or "bio-heat" equation: $h_b = V \rho_b C_b (1-\kappa)(T_a - T)$, where $h_b$ is the rate of heat transfer per unit volume of tissue, V is the perfusion rate per unit volume of tissue, $\rho_b$ is the density of blood, $C_b$ is the specific heat of blood, k is a factor that accounts for incomplete thermal equilibrium between blood and tissue, $T_a$ is the temperature of arterial blood, and T is the local tissue temperature. Heat transfer from other sources is negligible for the purpose of this disclosure. Moreover, $\rho_b$, $C_b$, and $\kappa$ are generally constant. Therefore, the system may compute an estimate of $h_b$ and the rate of change of $h_b$ throughout the wash-in, equilibrium, and wash-out cycles. There is a tight link between cerebral temperature (T) and metabolic rate (CMR). That is, CMR generally slows as T drops. Moreover, heat produced by the brain is proportional to the CMR. Therefore, $h_b$ and CMR (including drug metabolic rate) at a temperature at a first time $T_{t1}$ will be lower than $h_b$ and CMR at a temperature at a second time $T_{t2}$, where $T_{t2}$ is greater than $T_{t1}$. The system may then calculate key cerebral hemodynamic characteristics (e.g., CBF, CBV, CVR, CPP, RPV, PST, PaO2, MAP, RSI, RHI, etc.) and/or metabolism characteristics (e.g., CMR, etc.) 112 based on at least one of heat $h_b$, perfusion rate V, and/or temperatures $T_a$ and/or T, wherein $T_a$ is determined from a reading from the one or more of the temperature sensors) during the wash-in and wash-out from a steady state cycles, as well as the amount of heat $h_b$ necessary to maintain tissue temperature of the brain from the measured native vessel flow rate of blood at equilibrium. Moreover, extraction fraction, CMR drug, and local drug toxicity may be manipulated by controlling one or more of heat $h_b$, perfusion rate V, and/or temperatures $T_a$ and/or T during drug delivery.

Brain heat production and removal in equilibrium may also be modeled with the following equation:

$$C_{tissue} \cdot \overset{\text{Final Brain}}{\underset{\text{Temperature}}{\dot{T}}} = \overset{\text{Brain Heat Production}}{(\Delta H^0 - \Delta H_b) \cdot rCMRO_2} - \overset{\text{Brain Heat Removal}}{\rho_B \cdot C_B \cdot rCBF \cdot (T - T_{arterial})}$$

where $C_{tissue}$ is specific heat of the brain, $\dot{T}$ is final brain temperature, $\Delta H^0$ is enthalpy per mol of oxygen, $\Delta H_b$ is energy that is required to release oxygen from hemoglobin, rCMRO2 is regional cerebral metabolic rate of oxygen, $\rho_B$ is density of blood, $C_B$ is specific heat of blood, rCBF is regional cerebral blood flow, and $T-T_{arterial}$ is the difference between brain temperature and arterial input temperature.

At rest, brain temperature is slightly higher than arterial temperature, approximately 37.3° C. vs. 37.0° C. This temperature equilibrium may be maintained at a very narrow range in most body systems (skin and extremities are exceptions). It is evident that heat removal increases with higher CBF and lower arterial input temperature (cooling). Both CMRO2 and CBF are temperature dependent and CBF is coupled to CMRO2 over a wide range of temperature, meaning CBF will change with changes in CMRO2: $q=q_0 \cdot \alpha^{\beta(T-37)}$ and $\omega=\omega_0 \cdot \alpha^{\beta(T-37)}$, where q is final CMRO2, $q_0$ is baseline CMRO2 at 37° C., $\alpha$ and $\beta$ are regression coefficients, (T−37) is new brain temperature, $\omega$ is final CBF, and $\omega_0$ is baseline CBF.

The cerebral hemodynamic and metabolism characteristics may be computed based on a two compartment model, using data collected and/or estimated during the wash-in and wash-out of cold to separate ischemic from non-ischemic tissue. That is, the information collected during the procedure using the arterial catheter may be used by the system to calculate estimates for cerebral metabolic rate ($^{est}CMR_{heat-combined}$), cerebral blood flow of normal tissue being perfused ($^{est}CBF_{normal}$), cerebral blood flow of penumbra tissue being perfused ($^{est}CBF_{penumbra}$), and cerebral volume of normal, penumbra, and dead tissue being perfused ($^{est}CV_{normal}$, $^{est}CV_{penumbra}$, and $^{est}CV_{dead}$, respectively), associated with the computed blood flows and preferably log/graph the estimates, without the need for tissue or venous measuring devices. Penumbra generally refers to ischemic tissue that has not irreversibly been injured. In this regard, the system may calculate both the blood flow of the tissue and the volume of the tissue associated with that blood flow. During controlled cooling or rewarming to a new temperature equilibrium (wash-in and wash-out), the blood flow is given by the slope of the plot of cerebral blood flow˜ (ml/min) vs. time, whereas the volume or weight of tissue (ml, grams) is given by the area under the plot. The ratio of these numbers gives the cerebral blood flow (mm/100 gr/min) As indicated herein, the estimates may be derived from regional cooling. The tissue volumes associated with regional cooling may therefore be the perfused volume of tissue (CV).

CV may be calculated as a function of (∫IR*T2− (IR$_{equilibrium}$*T2$_{equalibrium}$*time to equilibrium))/T1initial− T1equilibrium) until ΔnvFR/Δt=0, where IR is the infusion rate, and normalizing for 1 degree temperature change. That is, a target temperature is picked, followed by cooling and summation of all the IR*T2 less the maintenance dose IR$_{equilibrium}$*T2$_{equlibrium}$ until the ΔnVFR/Δtime reaches zero. This represents the area under the curve representing the plot of IR*T2 over time, followed by correction to 1 degree temperature change. This is the heat content of the volume of tissue perfused, and since 1 ml of tissue has 1 calorie of heat per degree, this approximates the volume of tissue perfused. T1 is the Admixture temperature, T2 is the temperature of the infusate, and T4 is the body temperature (° C.), nvFR is the native vessel flow rate, and t is time ... CBF$_{total}$ may be computed by dividing admFR by CV at equilibrium. Heat transfer from organs (other than the skin) is almost exclusively done thru blood flow. Additionally, because of the tight relationship between arteries and veins, there is a nearly invariant relationship between artery, tissue, and venous temperature. Therefore blood flow rate approximates heat transfer. Areas of brain having high flow rates will reach the new temperature equilibrium quickly whereas areas of brain having lower rate will do so slowly. The heat transfer to a new equilibrium temperature is an exponential function of blood flow.

Figure 4A:
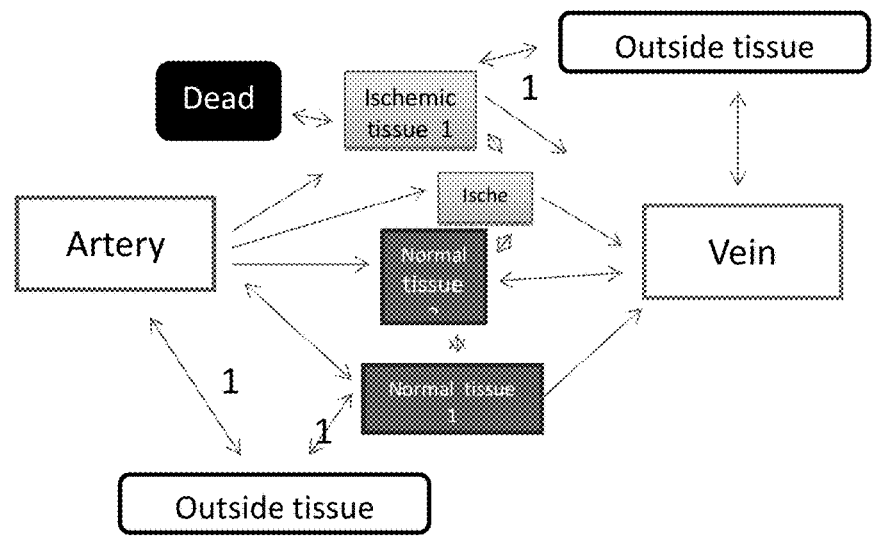
FIGS. 4a-4b depict a block diagram of a two compartment model for use in estimating metabolic rate of an organ.
Figure 4B:
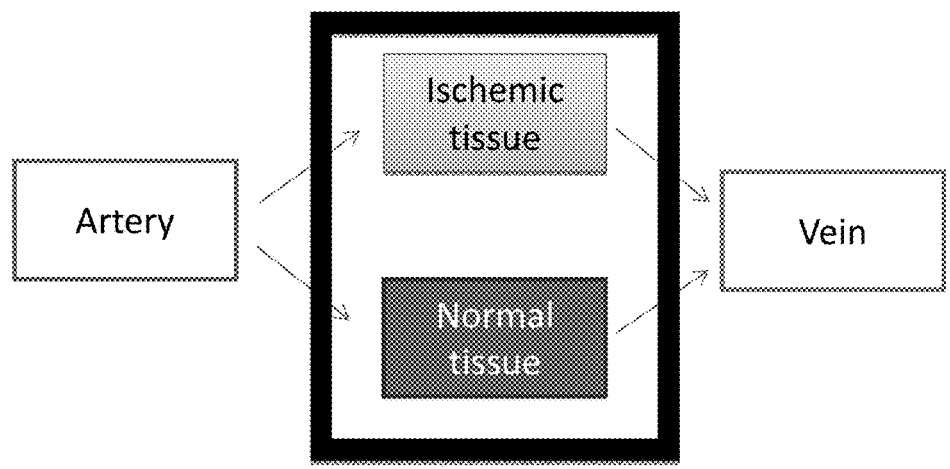

Referring to FIGS. 4a-4b, the two compartment model (ischemic vs. normal tissue, (or tumor vs. normal tissue) (the black box) represents the following assumptions: 1) near complete thermal isolation of the brain from outside tissue, 2) near complete heat flux between the arterial input and venous output, 3) insignificant heat flux between ischemic and normal tissue, 4) that there is one flow rate for all normal tissue and a second flow rate for all ischemic tissue, 5) changes in blood flow and heat transfer associated with changes in tissue temperature during the cooling phase can be ignored as they effect all parts of the system equally, and 6) dead tissue, i.e., the ischemic core, will minimally affect the measurements. Note, most type tumors have a distinctly different blood flows than the surrounding normal tissue and most have higher blood flows. Additionally, germane to IA drug dosing, tumors usually have a different partition coefficient than normal tissues, as well as breakdown of normal tissue/blood barriers.

The system may calculate $^{est}CBF_{normal}$, $^{est}CBF_{penumbra}$, $^{est}CBF_{ischemic}$ and $^{est}CV_{normal}$, $^{est}CV_{penumbra}$, and $^{est}CV_{dead}$ in one of a plurality of ways, including using a curve peeling approach and a two compartment analysis first differential equation approach.

The curve peeling approach assumes the vessel flow rates can be modeled as the sum of two exponentials, such that $C=C_1 \exp(-\lambda_1 t)+C_z \exp(-\lambda_z t)$. The values with subscript z may be calculated from the terminal phase portion of the curve, and C is the actual, measured flow rate at any particular time t. By determining $C_1$ and $\lambda_1$ one can find the total area under the curve (AUC) by integrating $C_1$ and $C_z$ separately with respect to t, and then taking the sum of these two values.

Generally, the process for computing normal and penumbra tissue characteristics proceeds as follows: i) a semi-log graph of flow rate may be plotted using gradient at large values of t to determine terminal phase constant of elimination, $\lambda_z$; ii) the terminal phase straight line may be projected back to t=0, using this line to calculate theoretical actual flow rate (i.e. not logged) for the time points that real data exists for; iii) values of $C_1=C-C_z$ may be calculated where C is the actual flow rate at any given time, and $C_z$ is the flow rate calculated from the terminal phase; iv) a semi-log plot of C1 against t may be constructed and the elimination constant from the gradient of this line at small values of t may be determined; and v) AUC=$C_1(t=0)/\lambda_1+C_z(t=0)/\lambda_z$ may be used to find total AUC.

Additionally, the heat produced by the brain (CMR$_{heat}$) equals: heat leaving brain−brain heat entering brain, at equilibrium. The heat entering the brain is generally equal to the heat transfer associated with arterial blood flow (AdFR*T1), and by the rule of continuity that this volume of blood entering the brain is equal to the volume of blood leaving the brain by the venous side. Moreover, we know from experimental data and suggested by the Pennes heat equation that the venous blood temperature is nearly constant at 0.2-0.3 C.° above the arterial blood temperature. Additionally, having previously calculated the volume of tissue that is being perfused, it is possible to estimate the CMR for the volume of perfuse tissue: $CMR_{heat}=((AdFR*(T1+0.25))/CV)$.

Additionally, it is known that CMR is constant and closely linked to temperature and blood flow. Repeated measurement at different temperatures, and/or variances from expected can be used to estimate additional useful metrics, such as $^{est}CMR_{heat-normal}$, $^{est}CMR_{heat-penumbral}$, ($^{est}CMR_{heat-tumor}$), etc.

The penumbral sparing threshold for temperature (PST) can also be found (i.e., the temperature for penumbral tissue that would lower metabolic demands thereof so that the metabolic demands could be met by the lower blood flow in the penumbra tissue ($CBF_{penumbra}$)). The PST can be found using reference tables based on a single measure or it can be found based measures taken by repetitively and incrementally lowing (or raising) the target temperature of the brain. That is, a target temperature may be picked followed by cooling and summating all the IR*T2 until the ΔnVFR/Δtime reaches zero. This is repeated at different temperatures and the CBF for each for each temperature is determined. The inflection point between exponential curve and horizontal is the Penumbral Sparing Threshold for tissue ($PST_{map}$).

The $PST_{temp}$ is the temperature at which the volume of the estimated penumbra tissue is zero. This is the temperature at which the metabolic demand and the blood flow of the tissues are met. Specifically: $PST_{temp}=T1$ temp when $CV_{penumbra}=>0$. (This is preferably offset by an apparent growth in $^{est}CV_{normal}$). Additionally, the penumbral sparing threshold for arterial pressure ($PST_{MAP}$) can also be calculated. To do so, the cerebral vascular resistance of the penumbral tissue ($CVR_{penumbra}$) and normal tissue may be calculated/measured first. The MAP needed to bring the $CBF_{penumbra}$ to normal ($PST_{map}$) may be determined. One way to do this is as follows: $CBF_{normal}=MAP/CVR_{normal}$ and $CBF_{penumbra}=MAP/CVR_{penumbra}$; solving for MAP on both sides results in the following: $CBF_{normal}*CVR_{normal}=CBF_{penumbra}*CVR_{penumbra}$; then, $CBF_{normal}/CBF_{penumbra}=CVR_{penumbra}/CVR_{normal}$; the ratio of $CBF_{normal}/CBF_{penumbra}$ (both determined as described before) represents the necessary percent change in MAP to achieve $CBF_{normal}$. Hereby, MAP is preferably adjusted for ICP, which is, if not otherwise actively monitored and known, approximately 10 mmHg in normals. In this calculation, both the pre-cerebral resistance (plugged vessels going into the brain) and the brain vascular resistance at the tissue level. The $PST_{MAP}$ measure is the aggregate—of a series of resistors, the first very high, being for instance the proximal occlusion, the second maximally lowered, as the ischemic capillary bed. Repeated measurements as described for the $PST_{temp}$, or pharmacological measurements can experimentally support the $PST_{MAP}$ estimate. MAP can be manipulated pharmacologically to increase in MAP confirming the calculation, and also guiding therapy. Additionally a $PST_{O2}$ for the partial Pressure of $O_2$ needed to keep the penumbra alive, $PST_{O2}$ can be calculated, using the Blood $O_2$ content equation for one skilled in the art. Increase in partial pressure of O2 needed to deliver the requisite amount of O2 to the tissue is then calculated. This measure is envisioned useful if hyperbaric O2 would be considered as a therapeutic approach.

Figure 4C:
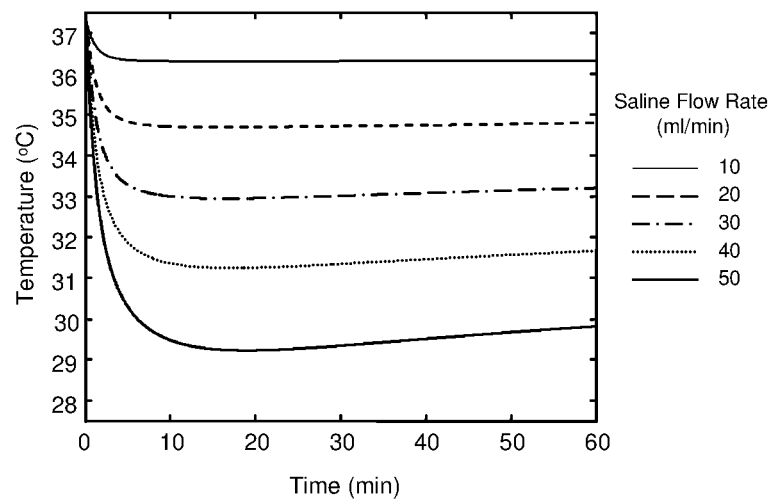
FIGS. 4c-4x depict graphs of hemispheric temperature changes of the brain during computer-simulated brain cooling, from testing on a bench model with simulated warm blood, and from a human study with selective brain cooling.
Figure 4D:
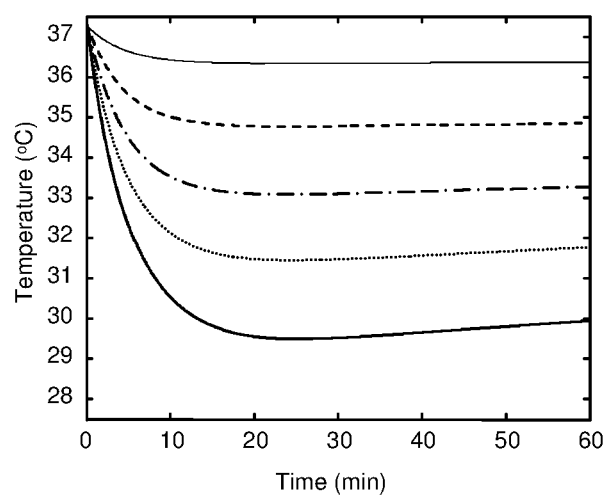
Figure 4E:
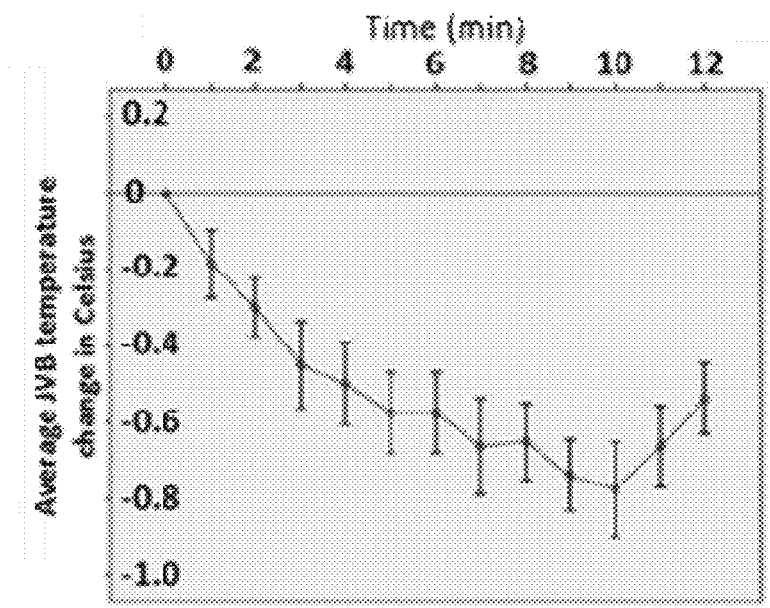
Figure 4F:
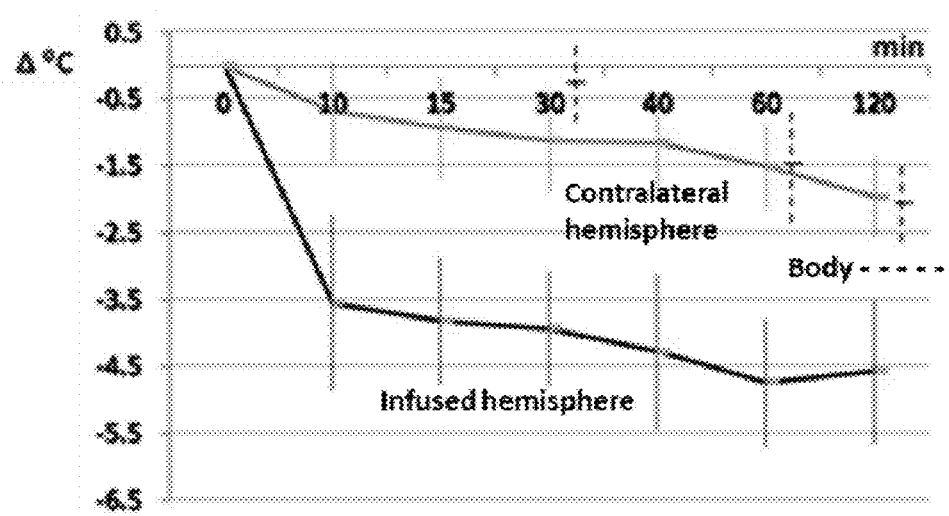

It is preferred that brain temperature changes as discussed herein occur quickly and are maintained without largely affecting other body systems. This may be achieved effectively by directly mixing cold physiological fluid (e.g. saline solution) with the blood in the internal carotid artery or ICA for instance, thereby modifying the arterial input temperature ($T_{arterial}$). FIGS. 4c-d depict a graphical simulation of brain hemispheric temperature changes with local cold saline infusion into the ipsilateral ICA. In this mathematical simulation: insulated catheter model, with cold fluid infusion at 5 different flow rates. FIG. 4e depicts temperature changes in a human study using regular catheter, non-insulated, with cold fluid infusion at 30 ml/min, temperature changes in the ipsilateral internal jugular vein. FIG. 4f depicts bilateral brain hemispheric temperature changes and body temperature changes with unilateral, local cold saline infusion into the ICA per manual control in a safety study in Pigs. A thermally insulated catheter and short fluid transit time through the catheter would allow only minimal heat transfer with the countercurrent aortic blood and enable fluid of low temperatures to mix with the blood in the ICA. This also minimizes the infused fluid volume. With this any brain selective hypothermic temperature in the mild to moderate range can be achieved in minutes.

Figure 4G:
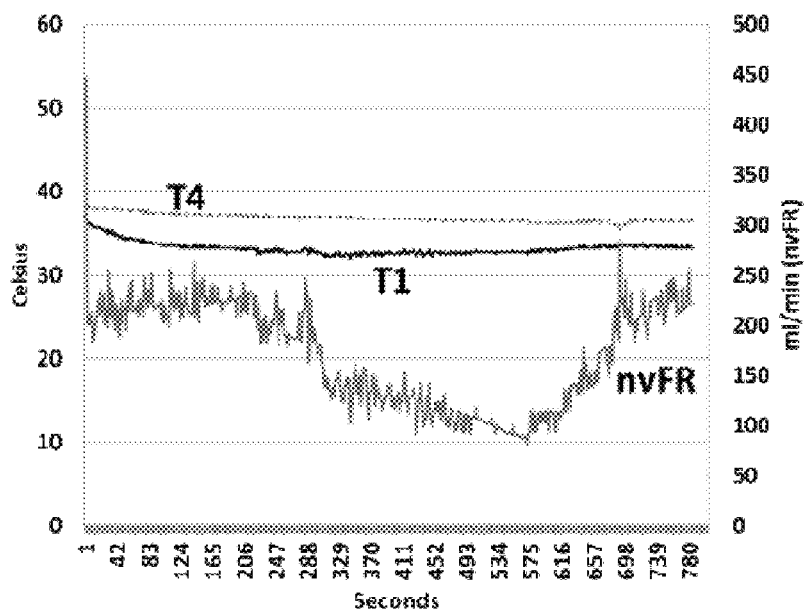
Figure 4H:
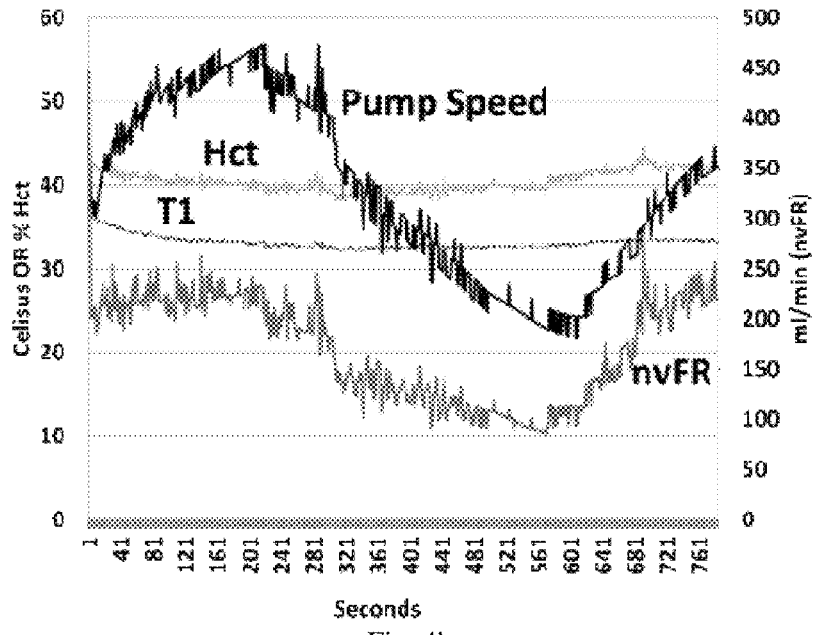
Figure 4I:
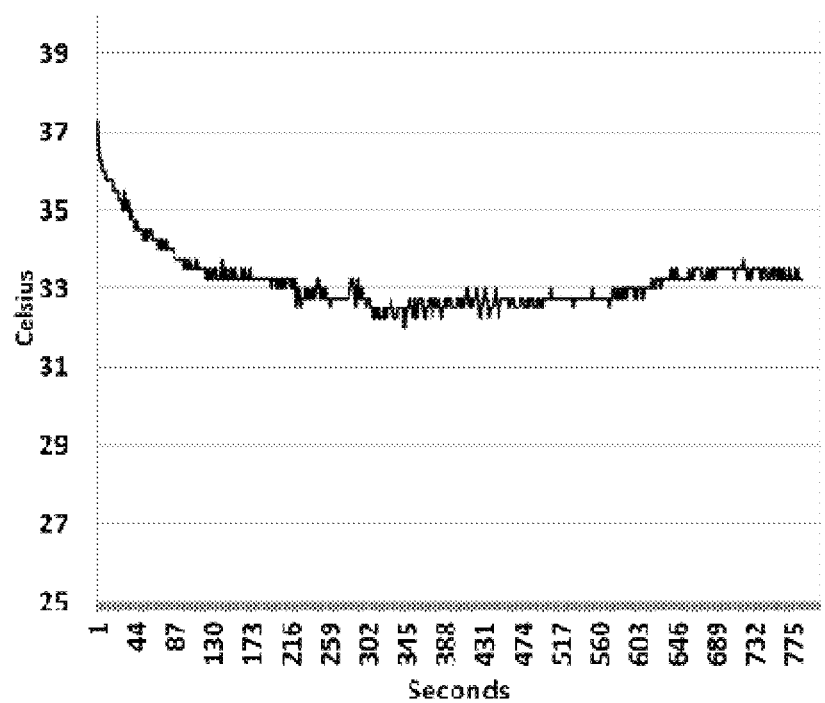
Figure 4J:
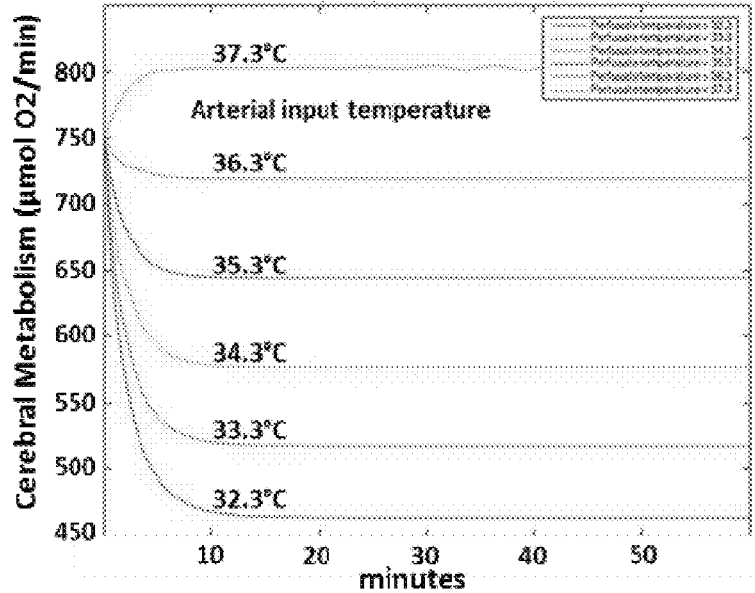
Figure 4K:
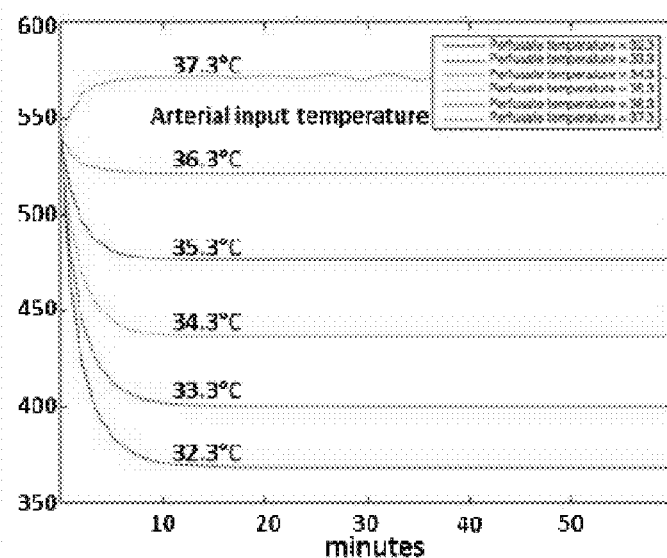

Because heat transfer between capillaries carrying 'cold' blood and 'warm' brain tissue happens rapidly, it is preferred to precisely control the arterial input temperature to which brain temperature will equilibrate with within minutes. The results of a vascular bench model experiment show that, despite the wide variation of simulated ICA blood flow (native vessel flow rate or nvFR) between 80 and 250 ml/min at 37° C., the present innovative algorithm quickly achieves target arterial input temperature ($T_{arterial}$) of 33° C. and maintains it precisely at an average 32.95±0.36° C., as shown in FIGS. 4g-i. The controller therefore preferably calculates the nvFR continuously based on temperature measurements at specific locations of the catheter and modifies the cold fluid pump rate to achieve and maintain $T_{arterial}$. In addition, arterial input hematocrit (measure of local hemodilution) is maintained within a normal range ensuring oxygenation remains sufficient. FIGS. 4g-i depict results of a controller test on vascular bench model with simulated blood circulation (nvFR=native vessel flow rate of the ICA at 37° C.). Target arterial input temperature (T1) of 33° C. was reached within 2-3 minutes and maintained precisely. Controller algorithm automatically adjusted cold fluid pump rate depending on measured nvFR in FIG. 4h. Arterial input hematocrit (Hct) stayed within physiological range (40% and above). Body temperature (T4) remained nearly constant as shown in the display of T1 trend in FIG. 4i.

Referring to FIGS. 4j-o, approximately 10-15% of a person's cardiac output is used for the cerebral circulation (~800 ml). Two ICAs supply the anterior cerebral circulation with blood (250-300 ml/min each) and two vertebral arteries (VA) connect to the smaller posterior circulation. Although the cerebral vasculature is interconnected through the Circle of Willis, the vascular territories are usually distinct from one another. Globally, cerebral perfusion does not change, although on a regional level activation of specific areas leads to a temporary rise in rCMRO2 and rCBF. Thus, normally blood flow in the ICA or VA is constant, regardless of the brain's activity.

Figure 4L:
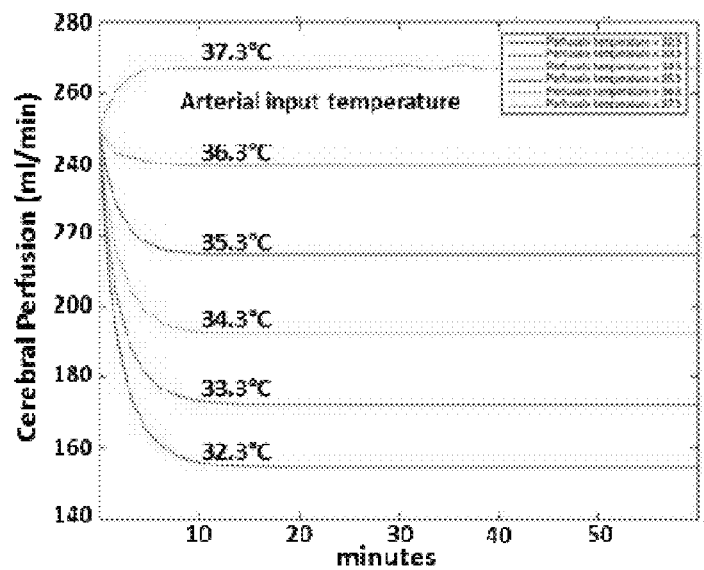
Figure 4M:
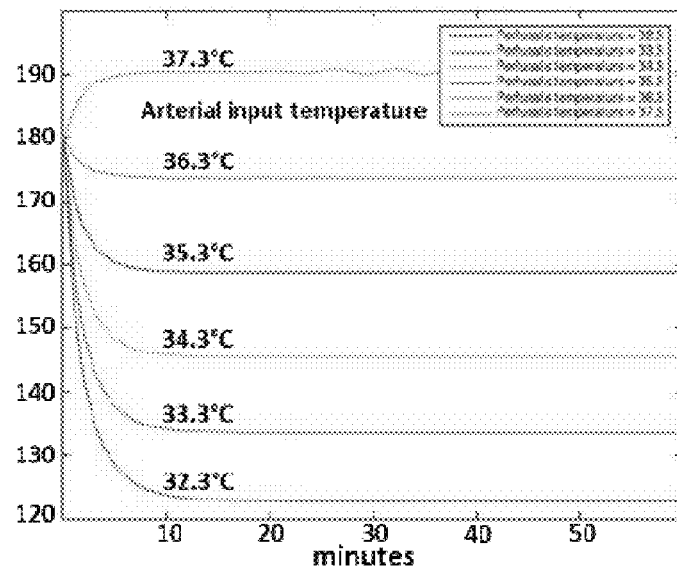
Figure 4N:
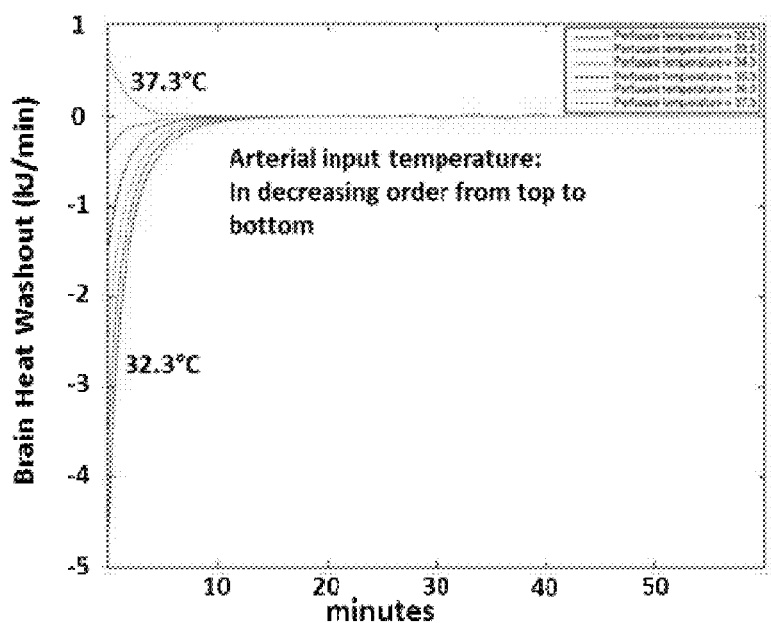
Figure 4O:
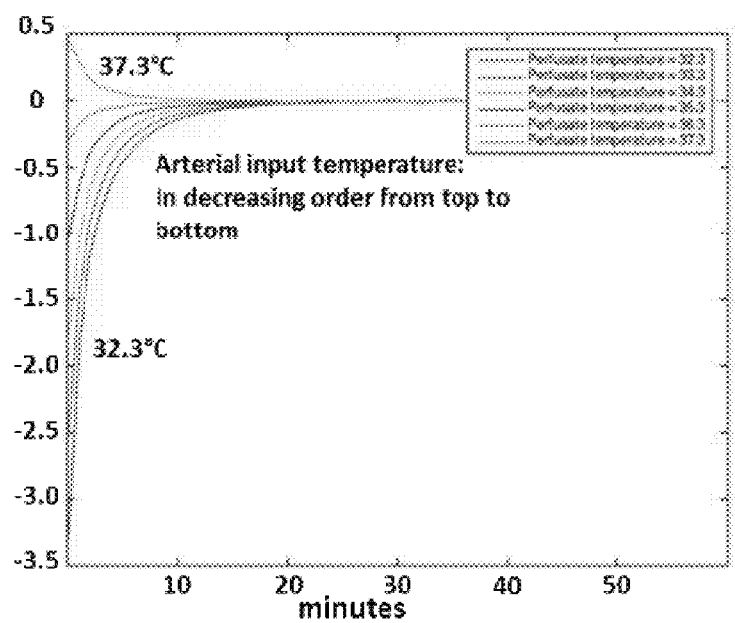
Figure 4P:
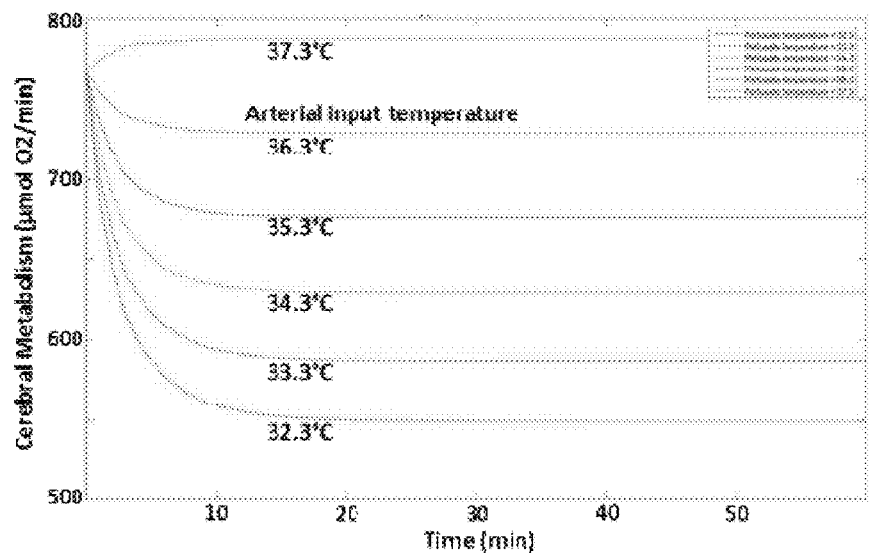
Figure 4Q:
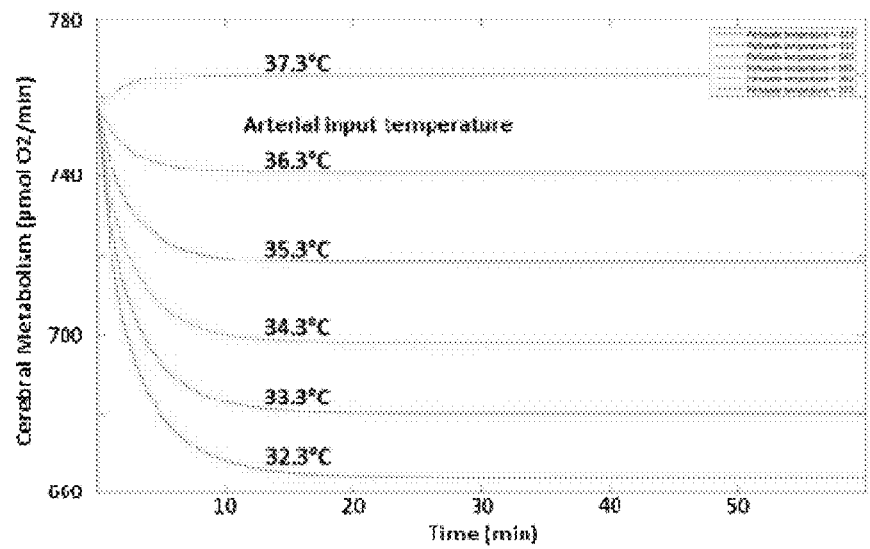
Figure 4R:
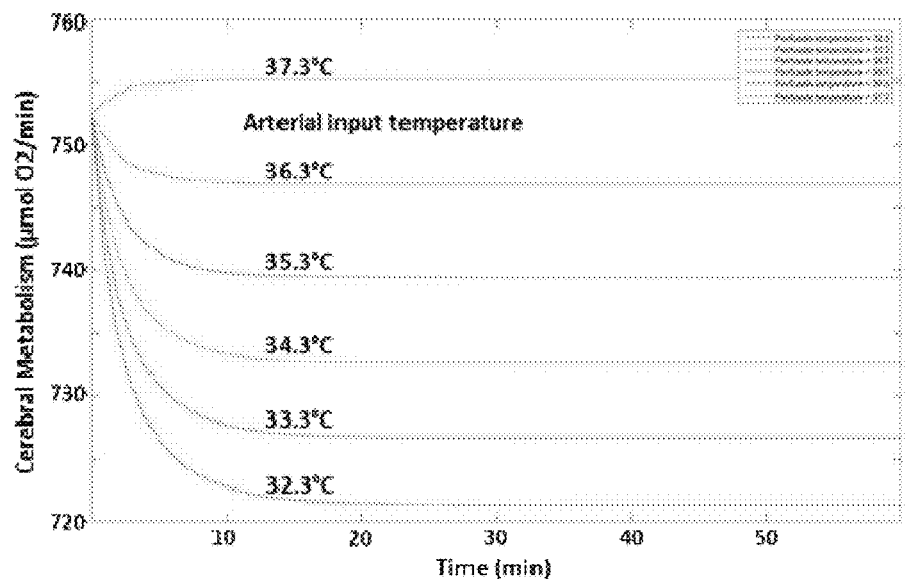
Figure 4S:
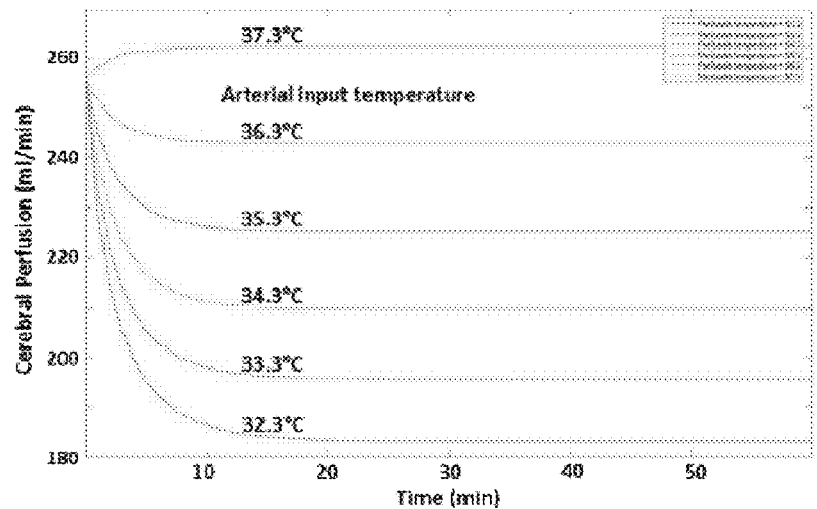
Figure 4T:
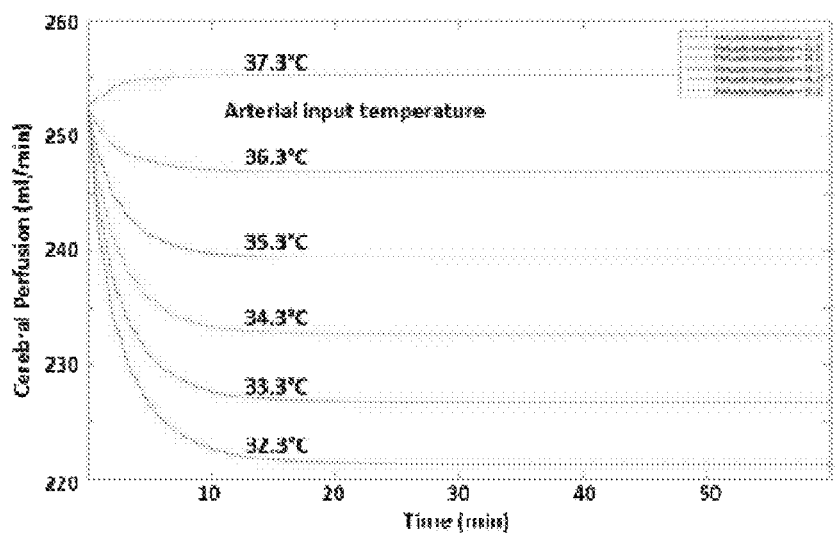
Figure 4U:
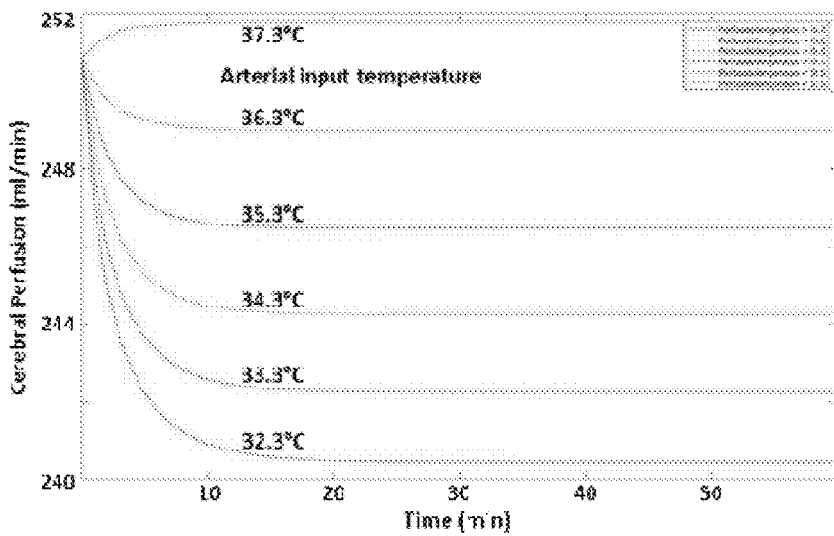
Figure 4V:
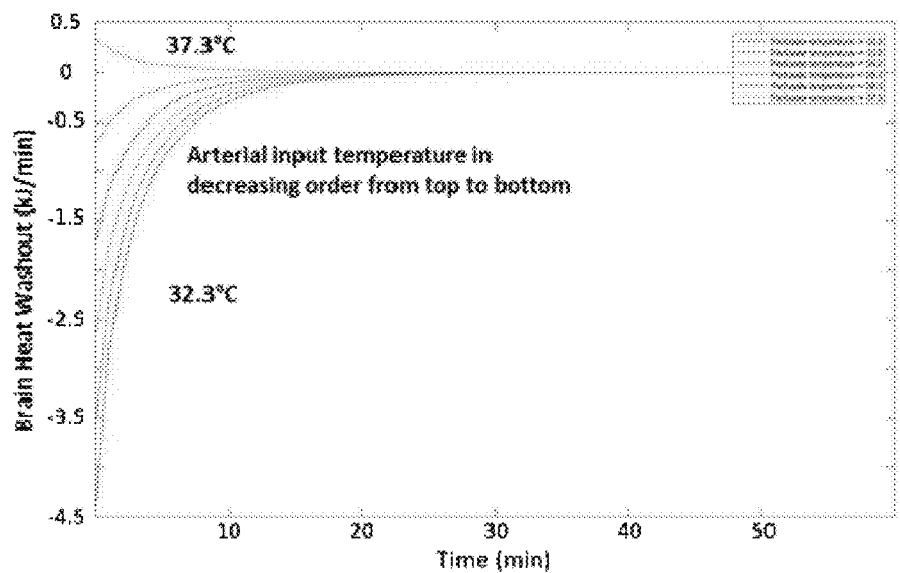
Figure 4W:
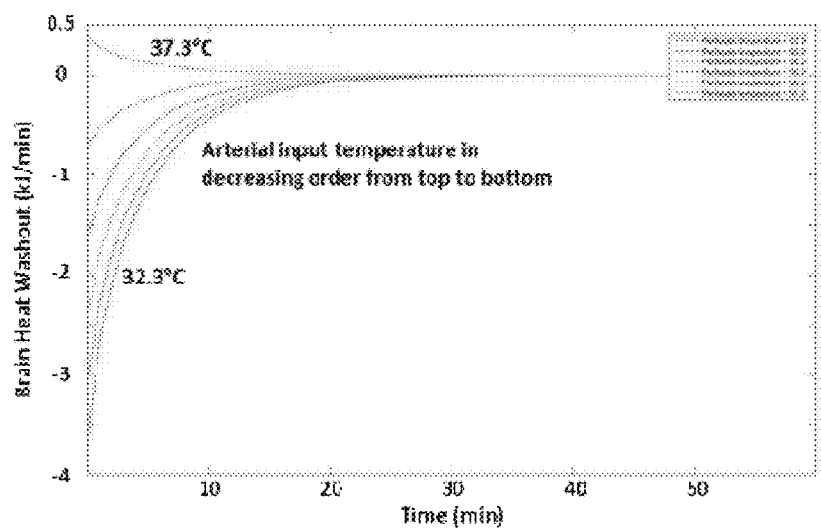
Figure 4X:
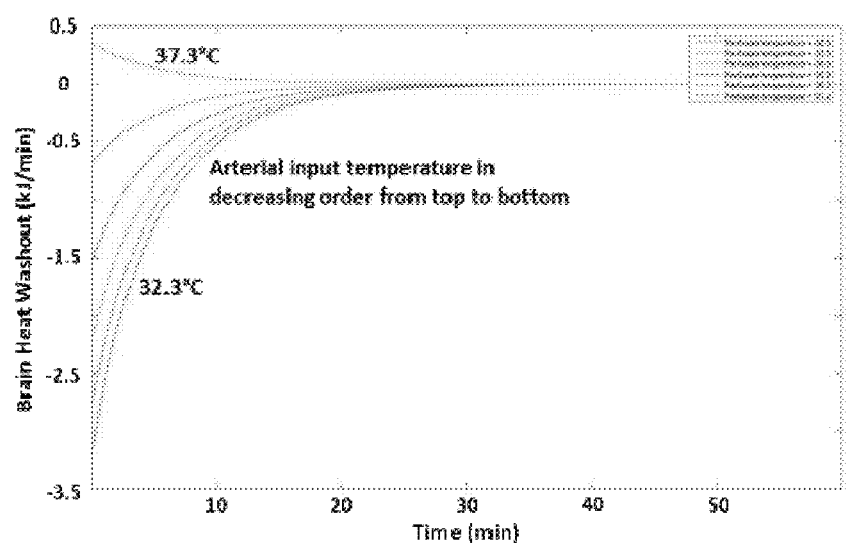

However, systemic blood gas changes alter brain perfusion, e.g. hypercapnia or hypoxemia will increase perfusion and vice versa. Similarly, an occlusion of the middle cerebral artery (MCA) will lead to a reduction of ipsilateral hemispheric perfusion, thus may result in reduced ipsilateral ICA blood flow (FIG. 4l-m). The corresponding values for oxygen metabolism and heat washout may be calculated (FIGS.

4j-o). Also, for intra-arterial cooling, collateral blood flow into the investigated hemisphere may result in prolonged duration to equilibrium, which will take longer the larger the proportional collateral flow (addition of another heat removal term with normal arterial blood temperature and multiplying with a fraction of total flow)(FIGS. 4p-x). Overall, this means that tracking ICA blood flow (nvFR) will give insight in the ipsilateral brain's anterior circulation perfusion. Each curve can be distinguished from another by its slope, timing, and integral value.

In FIGS. 4j-o, changes in brain oxygen metabolism (j/k), perfusion (l/m), and heat washout (n/o) at different levels of selective brain cooling were simulated. Simulation was performed as follows: brain of 500 g was perfused with blood at 5 different arterial input temperatures (37.3° C. to 32.3° C.); baseline input temperature is 37.0° C.; plateaus are reached within 10 minutes that indicate temperature equilibrium between arterial blood and brain has been reached. Graphs c, e, and g represent 500 g normal brain; graphs d, f, and g represent an ischemic brain with 300 g normal and 200 g ischemic compartments; baseline and ischemic CMRO2 are 150 µmol and 45 µmol O2/100 g/min, perfusion is 50 ml and 5 ml/100 g/min, respectively. The difference in temporal trends between normal and ischemic brain up to the point of equilibrium is shown in the following Table B.

| Perfusate Temperature (° C.) | Δ A-B µmol/min | Δ C-D ml/min | Δ E-F kJ/min |
|---|---|---|---|
| 32.3 | 113.5 | 37.7 | −0.293 |
| 33.3 | 135.1 | 45.1 | −0.257 |
| 34.3 | 153.0 | 51.0 | −0.194 |
| 35.3 | 175.0 | 58.3 | −0.123 |
| 36.3 | 199.9 | 66.6 | −0.045 |
| 37.3 | 226.3 | 75.4 | 0.070 |

Referring to FIGS. 4p-x, simulation are shown of changes in brain oxygen metabolism (p/q/r), perfusion (s/t/u), and heat washout (v/w/x) at different levels of selective brain cooling and different levels of collateral blood flow, 30% (top row), 70% (middle row), and 90% (bottom row). Simulation was performed as follows: brain of 500 g was perfused with blood at 5 different arterial input temperatures (37.3° C. to 32.3° C.); baseline input temperature is 37.0° C.; plateaus are reached that indicate temperature equilibrium between arterial blood and brain has been reached. Baseline CMRO2 is 150 µmol/100 g/min and perfusion is 50 ml/100 g/min, respectively.

Figure 5A:
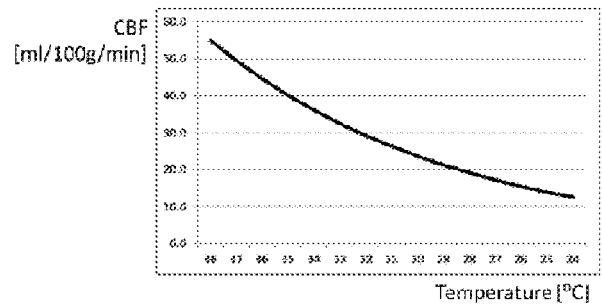
FIGS. 5a-f depict graphs of cerebral blood flow and metabolic rates in normal and ischemic tissue vs. temperature.
Figure 5B:
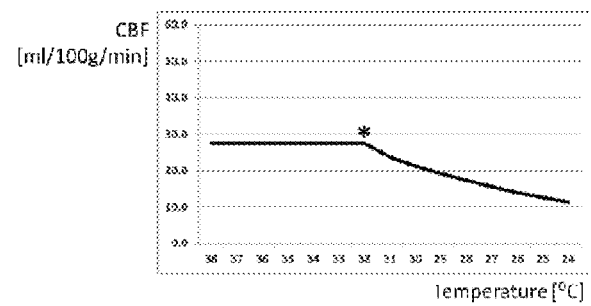
Figure 5C:
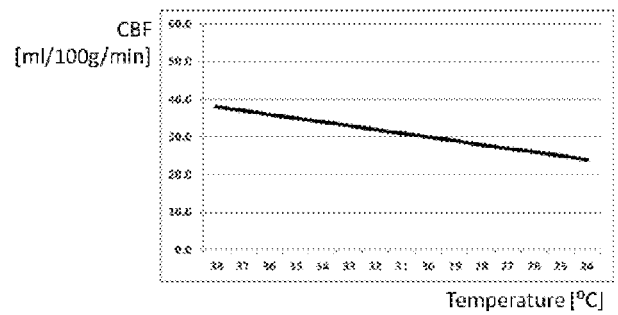

The perfusion data from an ischemic cerebral hemisphere contain information from two major compartments; one, the normal compartment ($P_n$) and two, the ischemic compartment ($P_i$). These two exponential phases can be curve-fitted in a linear fashion using log-graphs. Then the y-intercept of the fast component will reveal the perfusion value for $P_n$. The difference between total baseline perfusion and $P_n$ represents ischemic perfusion, $P_i$. The perfused tissue volume (via brain density) and weight ($P_i/CBF_i$) may be calculated. The accuracy of the calculated volumes may be improved by inserting a correction factor that will be higher toward extreme weight ratios of [$R_{weight}$=normal brain: ischemic brain Referring to FIG. 5a, the graph of temperature and cerebral blood flow in normal brain hemisphere shows that as the temperature of the tissue decreases, the cerebral blood flow decreases in an exponential fashion. In FIG. 5b, the graph of the ischemic penumbra tissue temperature and cerebral blood flow shows that the blood vessels will stay maximally dilated until the temperature is lowered to the point where the oxygen need can be met by the new temperature-adjusted metabolism and blood flow. Until then, the blood flow remains unchanged (horizontal portion of the line). This inflection point (*) is the Penumbral Sparing Threshold, PST, for temperature. After this point, CBF decreases again exponentially with decreasing temperature. In FIG. 5c, the graph of the combined normal and penumbra tissue shows that brains that have both normal and penumbral ischemic tissue, the curves will be a composite of the two graphs (5a and 5b).

Figure 5D:
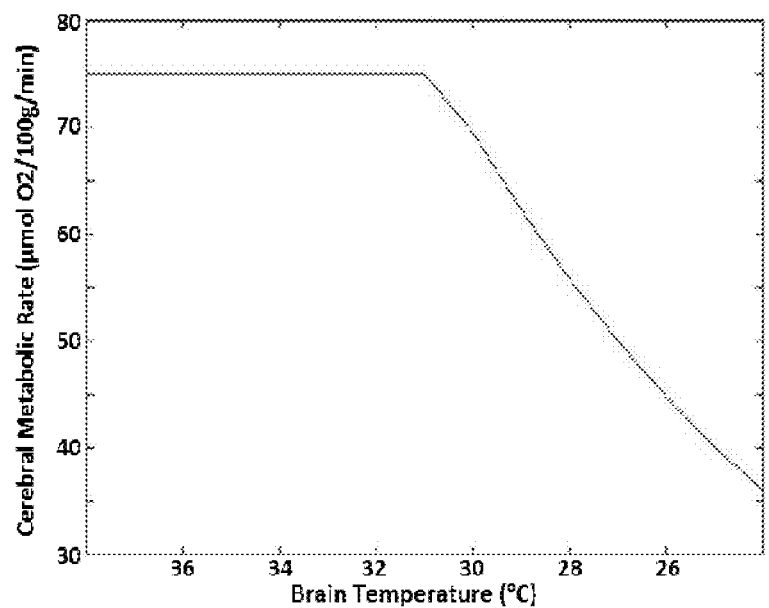
Figure 5E:
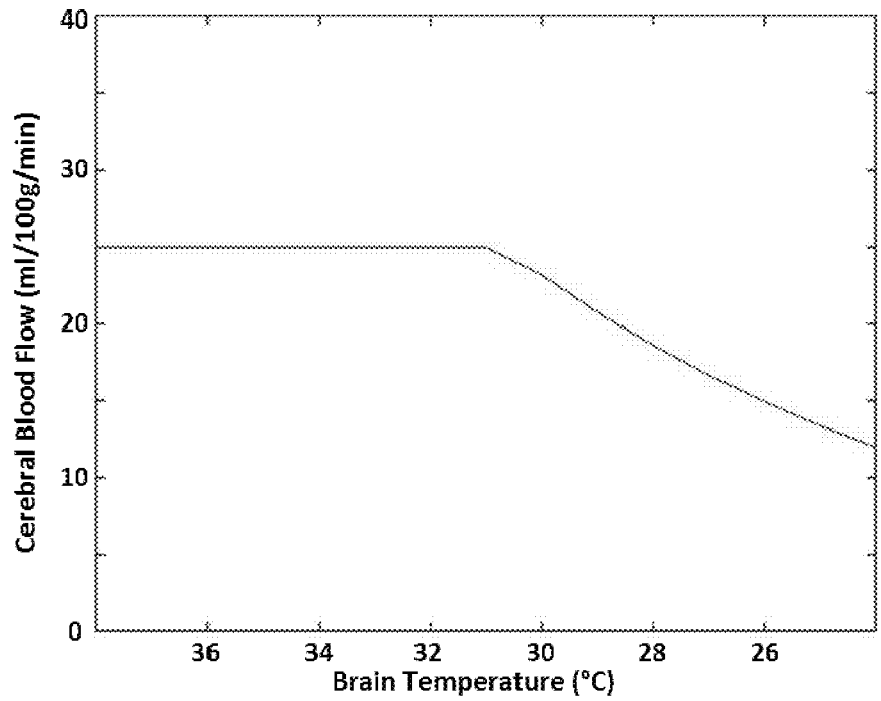
Figure 5F:
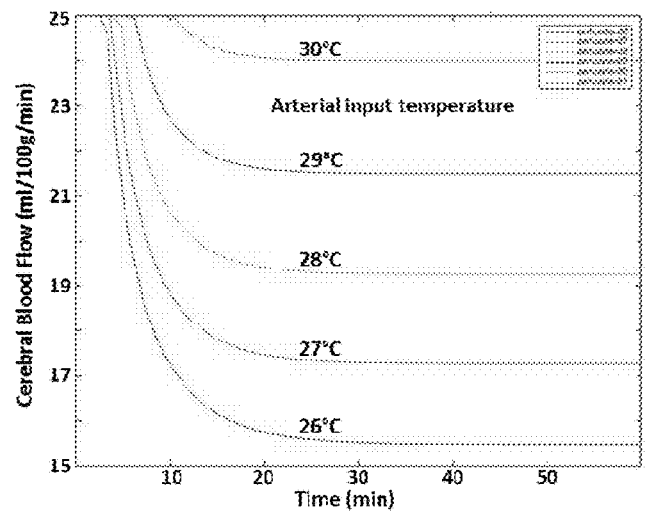

The present application therefore allows one to determine the temperature threshold for salvaging penumbral or ischemic brain tissue based on actual metabolic rate and blood flow. A further drop in tissue temperature below the threshold would provide hypothermic protection as shown in FIGS. 5d-e, which depict simulated temperature threshold for penumbral/ischemic brain tissue with [d] CMRO2 of 75 µmol O2/100 g/min and [e] CBF of 25 ml/100 g/min is 30° C., with decreasing tissue demand below temperature threshold. Ischemic brain tissue may require brain cooling to deep hypothermic levels. The present application would allow this to be performed safely and based on actual physiological tissue parameters as shown in FIG. 5f, which depicts a Simulated temperature threshold and CBF changes for penumbral/ischemic brain tissue with CBF of 25 ml/100 g/min, with decreasing tissue demand below temperature threshold.

Two new biomarkers disclosed in this patent are for the conditions of 1) Reperfusion Injury, and 2) Reperfusion Hyperemia. Both are seen in situations where there is occlusion of a blood vessel followed by reperfusion. Clinically, in the past they have been hard to study, so the entire range and associations are not fully appreciated. Experimentally, much is known but the exact mechanisms are not fully understood. They are thought to be related to dysfunction and subsequent damage of the blood vessel lining that then causes damage, even the preponderance of damage after an ischemic episode. Methods for treatment are being explored and include hypothermia. Both conditions are related to each other. The former, Reperfusion Injury is a progressive damage of the blood vessels and tissue that occur following reperfusion leading to increased ischemia, edema, and cell death. Both phases of hyperperfusion (reperfusion hyperemia, luxury perfusion), and hypoperfusion (misery perfusion) have been observed following reperfusion in ischemic conditions. Hyperemia is an initial transient increase in blood vessel flow, followed by a return to a lower, more normal blood flow. There are likely normal and pathological types of this condition, and related to changes in autoregulation. Both indices are related to the blood flow measured immediately after reperfusion and the blood flow at a later time. Both use the native blood vessel flow, nvFR, described in this patent to calculate, to calculate a Reperfusion Hyperemia Index and/or Reperfusion Severity Index. Reperfusion Hyperemia Index may be calculated by taking the ratio of the subsequent peak nvFR after reperfusion, over the immediate peak nvFR. The higher this score, the worse the hyperperfusion index. A score below one is suggestive of a missed reperfusion measurement, or severe reperfusion injury, and a no-flow state. Reperfusion Severity Index may be calculated by taking the ratio of the immediate peak nvFR over the subsequent lowest nvFR after reperfusion adjusted for time. The higher this score, the worse the hyperperfusion severity index. The more delayed the time to the second measurement the higher confidence. When only short time intervals are available for measurements additional indexes are envisioned that adjustments for the initial hyperemia.

It should be noted that although these calculations are for ischemic tissue vs normal tissue, they are equally germane to tumor vs. normal tissue. Additionally, use of these methods can be applied to determine cerebral vascular reserve in a similar ways with this device and method. (Increasing temperature, decreasing the Hct, etc.).

Other indices of ischemia or generally instances of vascular concerns can be derived using this information and real time assessment. For instance, short bursts of highly variable amplitudes seen in T2 can be associated with AIR-EMBOLI, missed by the previous in-line bubble detectors. The high frequency transients or spikes are related to changes in thermo-conduction, evaporation, movement, and electrolytic changes that are identified due to the tiny thermal inertia of the tiny thermocouples. Free standing tiny thermocouples, (0.003"×2), are sensitive to such perturbations, and pending on the liquid, bare thermocouples are significantly more sensitive. The tinier the thermocouple, the greater the sensitivity.

Figure 6:
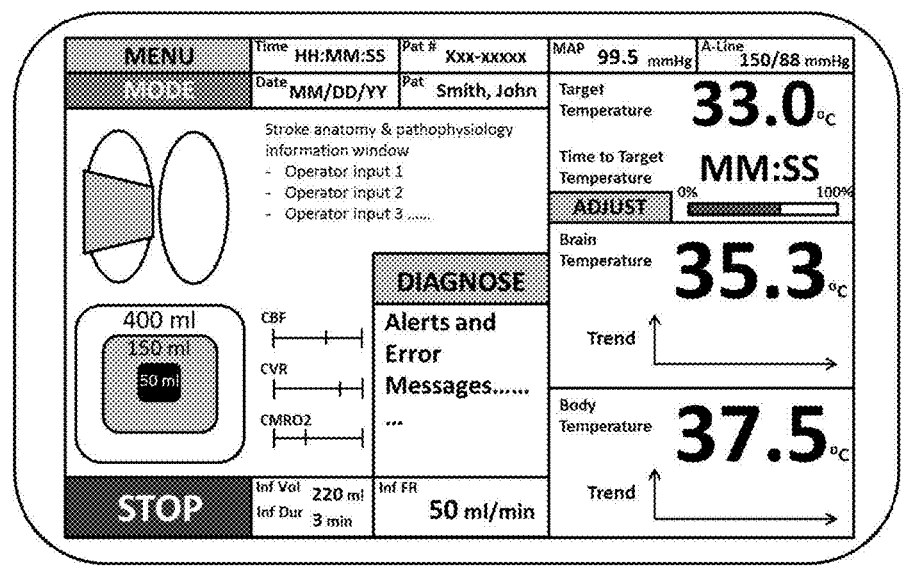
FIG. 6 depicts display screen generated by a system or use in estimating metabolic rate, blood flow, and vascular resistance of an organ according to at least one embodiment of the systems discussed herein.

The variables measured and/or estimated herein may be collected and displayed by the system, for example, in real time, in a display screen, such as that shown in FIG. 6. Referring to FIG. 6, the interface screen may display various variables, such as the date, time, patient number (ID) and name. The screen may further display physiological variables of the patient obtained, for example, with the one or more sensors on the insertion device or otherwise, such as mean arterial pressure (MAP), arterial line pressure (A-Line Pressure), body temperature, organ (brain) temperature, etc. The display may also include graphics showing the trend of the variables, such as with arrows showing the brain and/or body temperature increasing or decreasing over time. The system preferably displays target settings and operating parameters. For example, the target temperature and time to target temperature may be set/determined and displayed on the interface screen, as well as parameters associated with infusion volume, duration, and rate Importantly, the system displays computed variables, such as the CBF, CVR, CMR, or any other variable disclosed herein, in real time. In instances where regional cooling is being performed, a graphic of the organ and the portion of the organ being perfused may be indicated, as shown in FIG. 6 with a hemisphere of the brain highlighted. In a preferred embodiment, the system computes $^{est}CV_{penumbra}$, $^{est}CV_{normal}$, and/or $^{est}CV_{dead}$, and displays these variables in real time on the display. As indicated above, as the brain temperature approaches a PST, the $^{est}CV_{penumbra}$ will approach zero. For example, the 150 ml shown in the display will decrease in real time to as low as 0 ml while the $^{est}CV_{normal}$ approaches the maximum 550 ml. The graphic showing the relative volumes of normal and penumbra will preferably adjust automatically to reflect the proportional change during the perfusion induced temperature changes discussed herein. Finally, the data collected may be used by the system to identify automatically specific conditions and graphics of those conditions in the display screen, such as alters.

As indicated above, the systems disclosed herein may be used during intra-arterial drug delivery to ultimately control drug effectiveness vs. toxicity. A variety of variables may be controlled in this regard, including drug dose, blood infusion temperature, and Hct, which in turn influence blood flow, drug concentration, and tissue metabolic rate. That is, the cooling catheter may be placed in the vessel whose vascular territory will be given the drug. The territory is interrogated using the system as described above to obtain baseline values of vessel blood flow, temperature, $CBF_{total}$ (if possible $CBF_{normal}$ vs. $CBF_{pathological}$), CMR, and admixture Hct.

Drug effectiveness vs. toxicity is in part determined by the drug dosage at the target, which in turn is effected by a number of variables, including drug transport half-life, extraction fraction, and specific tissue drug toxicity. The system disclosed herein may address these three issues during intra-arterial drug delivery by inducing desired changes to the physiological characteristics of the organ followed by intra-arterial drug administration. Specifically, extraction fraction (EF) may be determined based on the transit time of the drug, tT, the surface membrane permeability (SMP), the drug concentration difference across the artery to vein (ΔAV), and the partition coefficient (PC) as follows:

$$EF=\int_0^t tT(SMP)(\Delta AV)(PC)$$

Therefore, the system of the present application can control EF by manipulating at least one of tT and ΔAV. Moreover, drug toxicity may also be mitigated by lowering the metabolic rate of the organ which results from a corresponding lowering of the tissue temperature. Finally, the drug dose, blood infusion temperature, and Hct, may be manipulated, thereby manipulating the blood flow, drug concentration, and tissue metabolic rate.

The present invention is described in the following Examples, which are set forth to aid in the understanding of the invention, and should not be construed to limit in any way the scope of the invention as defined in the claims which follow thereafter.

EXAMPLE 1

In one embodiment, the system will provide the following information essentially immediately once the catheter is in place, e.g., in the internal carotid artery (ICA): T1 (local blood temperature, before cold infusion); T4 (core body temperature); AP (arterial blood pressure when hooked up to an a-line pressure monitor); MAP (mean AP, calculated from AP over time: MAP=[(2×diastolic)+systolic]/3).

The following information may be made available within a very brief period (seconds) of cold infusion: —cold infusion temperature ($T_{input}$); cold infusion flow rate (IR) and volume (infV); T1 (admixture temperature); T2 (distal cold infusion temperature); T4 (core body temperature); AP (arterial blood pressure when hooked up to an a-line pressure monitor); MAP (mean AP, calculated from AP over time: MAP=[(2×diastolic)+systolic]/3); nvFR (native vessel flow rate, e.g., of the ICA, MCA, ACA, PCA etc., thermodilution method); and nVR (native vascular resistance: nVR=MAP/nvFR).

For diagnostic purposes, the organ, e.g., the brain, target temperature will be set, e.g., decrease of 2° C., i.e., 35.5° C., if baseline is 37.5° C. The controller may then infuse cooled fluid into the brain thereby cooling organ tissue. The target temperature will not be reached in one step, but in several steps, e.g., 0.5° C. at a time. For each step the controller adjusts infFR based on measured nvFR until nvFR remains constant at which point target organ temperature has been reached (temperature equilibrium between admixture and target organ). At this point the total amount of cooling will be determined (negative calories).

The underlying physiological principles are that CBF (cerebral blood flow) is determined by CMRO2 (cerebral oxygen metabolism), which is determined by temperature.

The graph with x=time [min or sec] and y=estimated organ temperature [° C.] is an exponential decay function determined by CMRO2, CBF, and temperature of the perfused part of the brain (tissue volume). Normal values for CMRO2, CBF, and brain temperature are known. Also known are admixture temperature and volume. The following additional information will be available with a short period (<1-3 minutes) of cold infusion into an organ-vascular territory, e.g. brain: Total cooling required to cool tissue to a known temperature ((−)cal); Tissue heat content of perfused volume ($HC_{tissue}$); Volume of perfused tissue ($V_{tissue}$); Estimated $CBF_{tissue}$; Estimated $CMRO2_{tissue}$ and $CMRglu_{tissue}$ (cerebral glucose metabolism) of perfused tissue; and Rough estimate of CVR (cerebrovascular resistance): CVR=CBF/MAP.

For therapeutic procedures, e.g., in acute ischemic stroke, this information may be obtained in one sequence. The target temperature will be set, e.g., decrease of 5° C., i.e., 32.5° C., if baseline is 37.5° C. The controller then infuses cooled fluid into the brain thereby cooling the organ tissue. The target temperature may be be reached in one step keeping T1 at the target temperature until nvFR is constant and remains constant at which point target organ temperature has been reached (temperature equilibrium between admixture and target organ). This follows the physiological principles that CBF (cerebral blood flow) is determined by CMRO2 (cerebral oxygen metabolism), which is similarly determined by temperature. The graph with x=time [min or sec] and y=estimated organ temperature [° C.] is an exponential decay function determined by CMRO2, CBF, and temperature of the perfused part of the brain (tissue volume). Normal values for CMRO2, CBF, and brain temperature are known. Also known are admixture temperature and volume. The following additional information will be available with a short period (<1-3 minutes) of cold infusion into an organ-vascular territory, e.g. brain: Tissue heat content of perfused volume ($HC_{tissue}$); Estimated Volume of tissue ($V_{tissue}$); Estimated $CBF_{tissue}$; Estimated $CMRO2_{tissue}$ and $CMRglu_{tissue}$ (cerebral glucose metabolism) of perfused tissue; and Rough estimate of CVR (cerebrovascular resistance): CVR=CBF/MAP.

At the end of the therapy, the brain may be allowed to return to baseline in sequential steps. The brain, target temperature may be set, e.g., increase of 1° C., i.e., to 33.5° C., if baseline is 32.5° C. The controller may then infuse cooled fluid into the brain and allow the brain to rewarm. The target temperature will not be reached in one step, but in several steps, e.g., 0.5° C. at a time. For each step the controller adjusts infFR based on measured nvFR until nvFR remains constant at which point target organ temperature has been reached (temperature equilibrium between admixture and target organ). At this point the total amount of cooling required will be determined. This follows the physiological principles that CBF (cerebral blood flow) is determined by CMRO2 (cerebral oxygen metabolism) which is determined by temperature. The graph with x=time [min or sec] and y=estimated organ temperature [° C.] is an exponential decay function determined by CMRO2, CBF, and temperature of the perfused part of the brain (tissue volume). Normal values for CMRO2, CBF, and brain temperature are known. From this data the Penumbra Sparing Threshold, PST, can be determined. This is based on the principle that as the temperature falls, the metabolic rate falls, and the blood requirements fall proportionally. Given a low enough temperature, creating a low enough metabolic demand for blood—the supplied blood that is sufficient to maintain a physiological metabolism—hence the metabolic penumbra is spared from ischemic injury.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A system comprising:
    a controller;
    an insertion device comprising at least one temperatures sensor thereon, the insertion device functionally coupled to the controller to provide a plurality of temperature measurements of a subject's organ to the controller;
    a pump functionally coupled to the controller for the controller to vary an infusate flow rate to induce temperature changes in at least a portion of the subject's organ, in accordance with at least one of a wash-in and a wash-out cycle, in which the controller varies the pump to induce temperature changes of at least a portion of the subject's organ between a first temperature and a second temperature in a sequence that comprises at least one of raising and lowering the temperature of the organ to at least one step temperature that is between the first and second temperatures, and maintaining the step temperature and at least one of the first and second temperatures for a given time;
    a memory device functionally coupled to the controller, the controller operable to store the plurality of measurements of the temperature of the subject's organ to the controller, taken throughout the at least one of the wash-in and wash-out perfusion induced temperature changes in at least a portion of the subject's organ, and further operable to estimate values for at least one hemodynamic characteristic of at least a portion of the subject's organ based on the plurality of temperature measurements obtained during the perfusion induced temperature changes and time as a variable.

2. The system of claim 1, wherein the at least one hemodynamic characteristic comprises a metabolic rate of at least a portion of the subject's organ.

3. The system of claim 1, wherein the at least one hemodynamic characteristic comprises a tissue blood flow rate associated with at least a portion of the subject's organ.

4. The system of claim 1, wherein the at least one hemodynamic characteristic comprises heat production associated with at least a portion of the subject's organ.

5. The system of claim 1, wherein the controller is operable to vary an infusate flow rate to lower the temperature in at least a portion of the subject's organ.

6. The system of claim 5, wherein the controller is operable to vary an infusate flow rate to maintain at least a portion of the subject's organ at an equilibrium temperature below normal.

7. The system of claim 6, wherein the controller is operable to vary an infusate flow rate to incrementally lower and decrease the temperature of at least a portion of the subject's to a plurality of different equilibrium temperatures, and to maintain the temperature of at least a portion of the subject's organ to each of the plurality of equilibrium temperatures.

8. The system of claim 7, wherein the at least one hemodynamic characteristic is estimated based on the plurality of temperature measurements during perfusion induced temperature changes comprising at least one wash-in, equilibrium, and wash-out cycle.

9. The system of claim 8, wherein the at least one hemodynamic characteristic comprises at least one of metabolic rate, a tissue blood flow rate, heat production of at least a portion of the subject's organ.

10. The system of claim 8, wherein the at least one hemodynamic characteristic comprises perfused volume of tissue.

11. The system of claim 8, wherein the at least one hemodynamic characteristic comprises perfused volume of penumbra tissue.

12. The system of claim 11, wherein the perfused volume of penumbra tissue is estimated as a function of a product of infusate rate and temperature at an initial time and at equilibrium.

13. The system of claim 8, wherein the at least one hemodynamic characteristic comprises blood flow associated with a perfused volume of tissue.

14. The system of claim 8, wherein the at least one hemodynamic characteristic comprises blood flow associated with a perfused volume of penumbra tissue.

15. The system of claim 8, wherein the at least one hemodynamic characteristic comprises a penumbra sparing threshold temperature.

16. The system of claim 8, wherein the at least one hemodynamic characteristic comprises a reperfusion hyperemia index.

17. The system of claim 8, wherein the at least one hemodynamic characteristic comprises a reperfusion severity index.

18. The system of claim 1, the controller further operable to display an interface screen comprising the at least one hemodynamic characteristic associated with at least a portion of the subject's organ.

19. The system of claim 18, wherein the interface screen comprises a real time display of at least one of infused volume of normal tissue and infused volume of penumbra tissue.

* * * * *